United States Patent
Gustafson

(10) Patent No.: US 10,441,272 B2
(45) Date of Patent: Oct. 15, 2019

(54) SUTURE MAGAZINE FOR SUTURE PASSING SURGICAL DEVICE

(71) Applicant: Medos International Sárl, Le Locle (CH)

(72) Inventor: Adam Gustafson, Rehoboth, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 226 days.

(21) Appl. No.: 15/637,413

(22) Filed: Jun. 29, 2017

(65) Prior Publication Data
US 2019/0000439 A1    Jan. 3, 2019

(51) Int. Cl.
| | |
|---|---|
| *A61B 17/04* | (2006.01) |
| *A61B 17/12* | (2006.01) |
| *A61B 17/06* | (2006.01) |
| *A61B 17/00* | (2006.01) |

(52) U.S. Cl.
CPC ...... *A61B 17/0469* (2013.01); *A61B 17/0401* (2013.01); *A61B 17/0485* (2013.01); *A61B 17/06061* (2013.01); *A61B 17/06133* (2013.01); *A61B 2017/00367* (2013.01); *A61B 2017/00407* (2013.01); *A61B 2017/0403* (2013.01); *A61B 2017/0409* (2013.01); *A61B 2017/0479* (2013.01); *A61B 2017/06042* (2013.01); *A61B 2017/06095* (2013.01); *A61B 2017/06142* (2013.01)

(58) Field of Classification Search
CPC . A61B 17/04; A61B 17/0469; A61B 17/0483; A61B 17/0485; A61B 17/0491; A61B 17/06061; A61B 2017/047; A61B 2017/0479
See application file for complete search history.

(56) References Cited

U.S. PATENT DOCUMENTS

| | | | |
|---|---|---|---|
| 5,368,599 A | 11/1994 | Hirsch et al. | |
| 5,454,822 A | 10/1995 | Schob et al. | |
| 5,871,490 A * | 2/1999 | Schulze ............. | A61B 17/0469 606/139 |

(Continued)

FOREIGN PATENT DOCUMENTS

| | | |
|---|---|---|
| EP | 0887045 A1 | 12/1998 |
| WO | 2013/130859 A1 | 9/2013 |
| WO | 2013/142487 A1 | 9/2013 |

OTHER PUBLICATIONS

Extended European Search Report for EP App. No. 18180332.1 dated Apr. 4, 2019 (12 pages).

*Primary Examiner* — Melanie R Tyson

(57) ABSTRACT

A surgical instrument for use in passing suture through tissue is provided that includes first and second jaws disposed on a distal end of an elongate shaft and configured to grasp tissue therebetween, and a needle selectively movable along a longitudinal channel extending through an outer side wall of the first jaw. The first jaw has a cavity configured to seat a removable and replaceable suture magazine. The suture magazine can be coupled to a suture magazine carrier that is removed before the surgical instrument is activated cause to the needle to advance distally and thereby pass a suture coupled thereto through tissue in a patient's body. As the needle is retracted proximally, a subsequent suture portion, such as a loop, is loaded onto the needle. The jaws remain in the body during passing the suture through the tissue.

20 Claims, 32 Drawing Sheets

(56) References Cited

U.S. PATENT DOCUMENTS

| | | |
|---|---|---|
| 6,605,096 B1 | 8/2003 | Ritchart |
| 6,770,084 B1 * | 8/2004 | Bain ................. A61B 17/0469 606/144 |
| 7,442,198 B2 | 10/2008 | Gellman et al. |
| 7,758,597 B1 | 7/2010 | Tran et al. |
| 7,879,048 B2 | 2/2011 | Bain et al. |
| 8,460,318 B2 | 6/2013 | Murray et al. |
| 8,562,629 B2 | 10/2013 | Bain et al. |
| 8,663,250 B2 | 3/2014 | Weber |
| 8,702,729 B2 | 4/2014 | Chu |
| 9,173,654 B2 | 11/2015 | Rush et al. |
| 9,220,497 B1 | 12/2015 | Lanois et al. |
| 9,247,938 B2 | 2/2016 | Martin et al. |
| 9,271,722 B2 | 3/2016 | Cournoyer et al. |
| 9,289,205 B2 | 3/2016 | Rohl et al. |
| 9,393,010 B2 | 7/2016 | Murray et al. |
| 9,427,228 B2 | 8/2016 | Hart |
| 2005/0288690 A1 | 12/2005 | Bourque et al. |
| 2007/0203507 A1 | 8/2007 | McLaughlin et al. |
| 2011/0118758 A1 | 5/2011 | Sauer |
| 2014/0222035 A1 | 8/2014 | Chu |
| 2015/0088167 A1 | 3/2015 | Chin et al. |
| 2015/0196294 A1 | 7/2015 | Murillo et al. |
| 2015/0351748 A1 | 12/2015 | White et al. |
| 2016/0135804 A1 | 5/2016 | Cournoyer et al. |
| 2016/0296225 A1 | 10/2016 | Rohl et al. |
| 2017/0020512 A1 | 1/2017 | Murillo et al. |
| 2017/0112487 A1 * | 4/2017 | Martin ............... A61B 17/0469 |

* cited by examiner

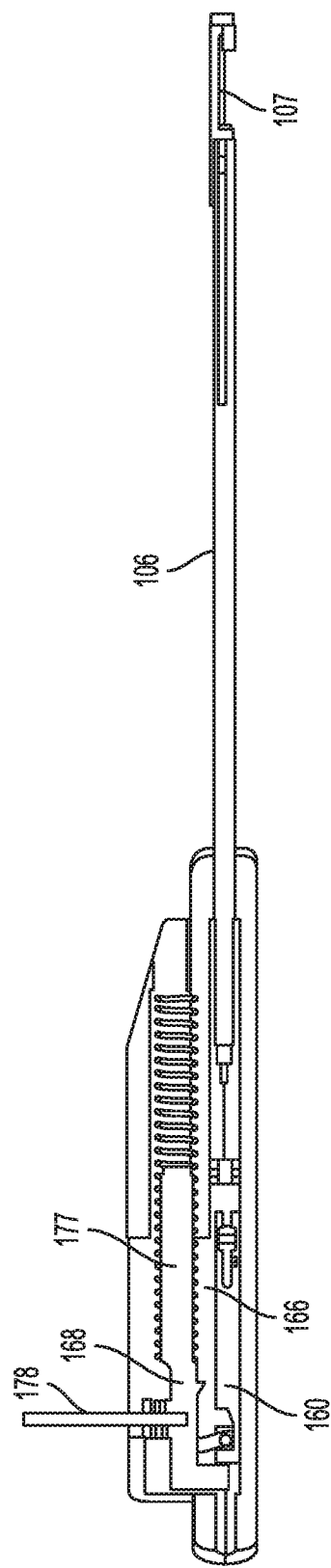

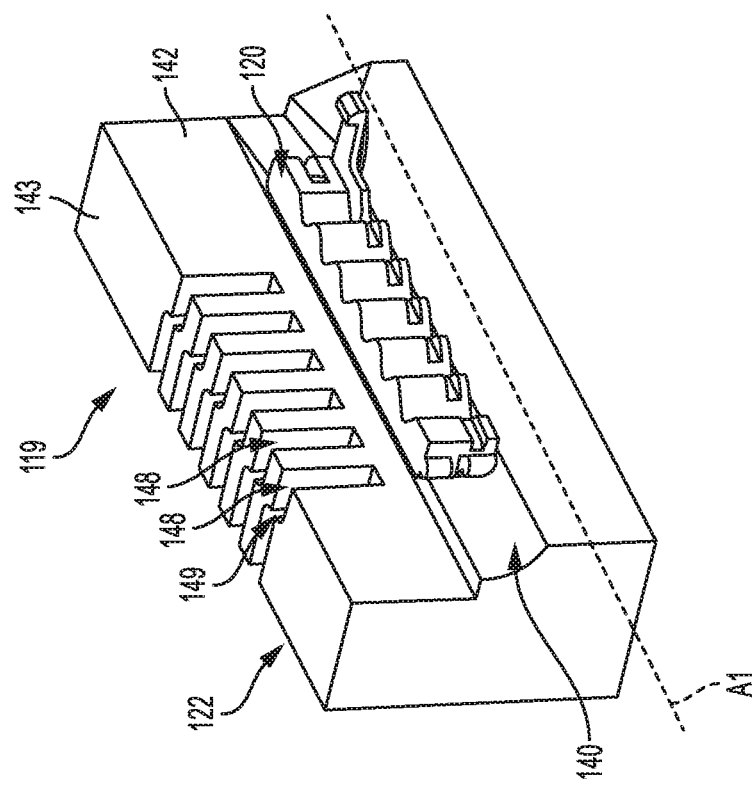
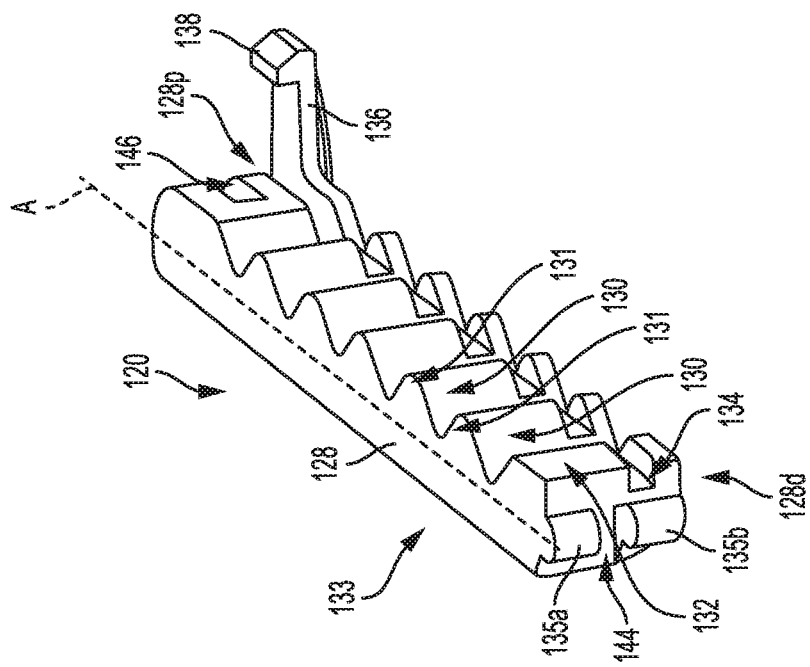
FIG. 6
FIG. 5

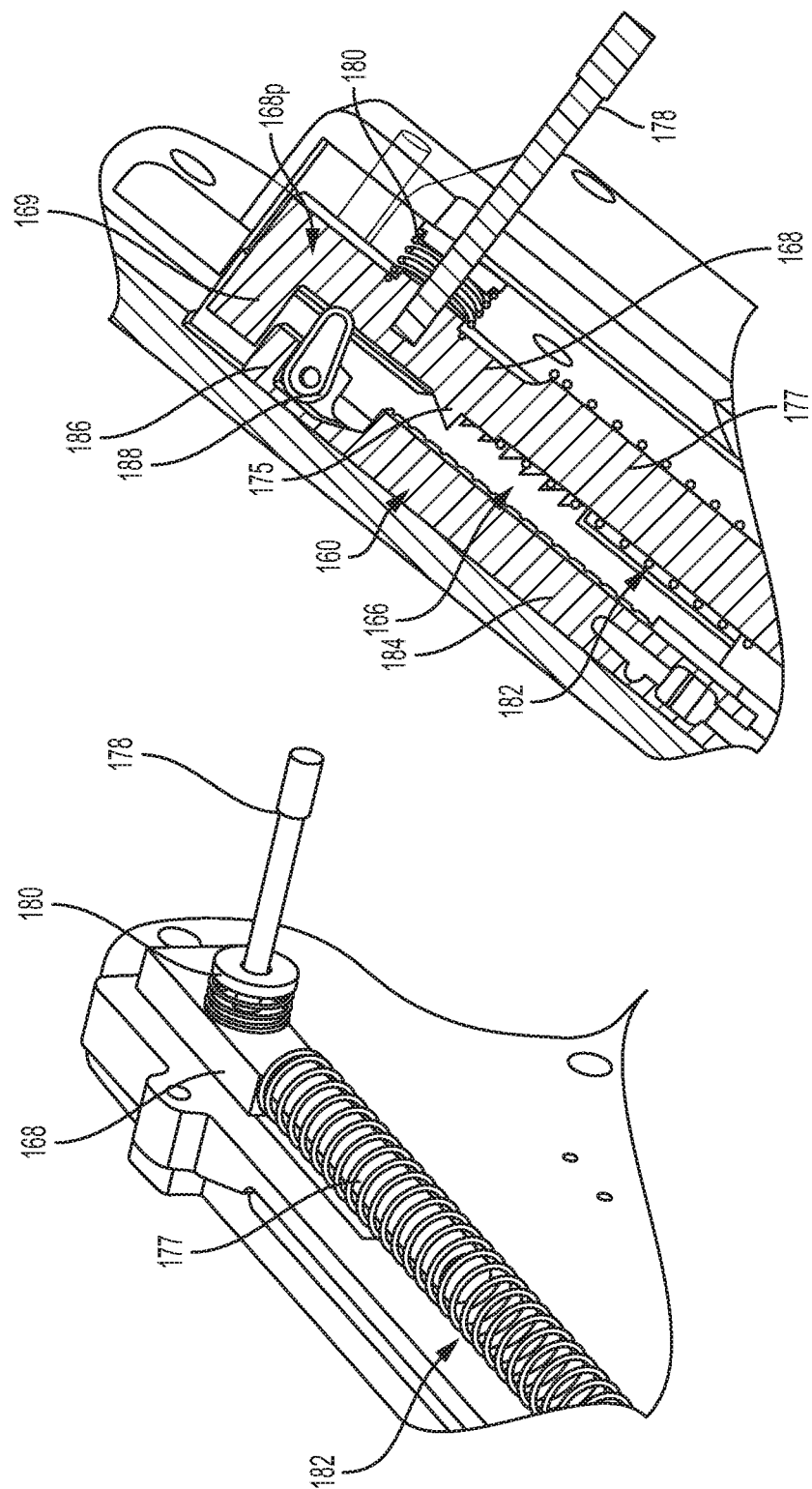

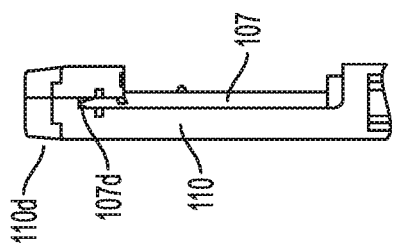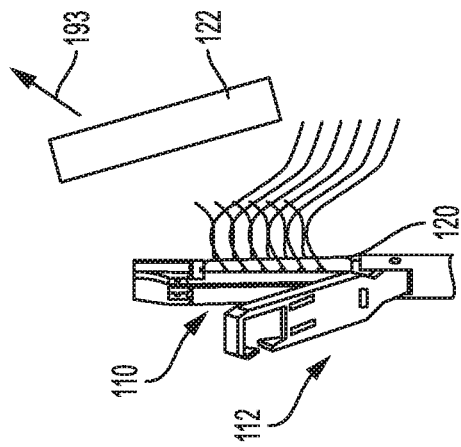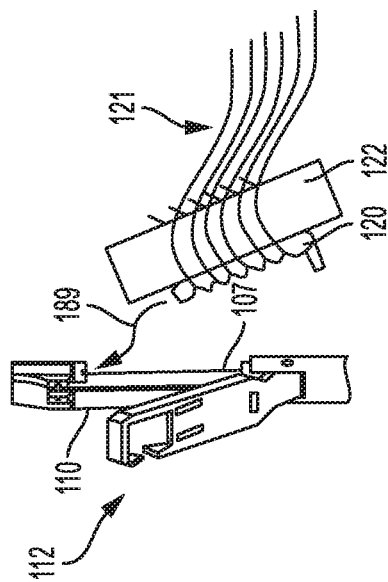

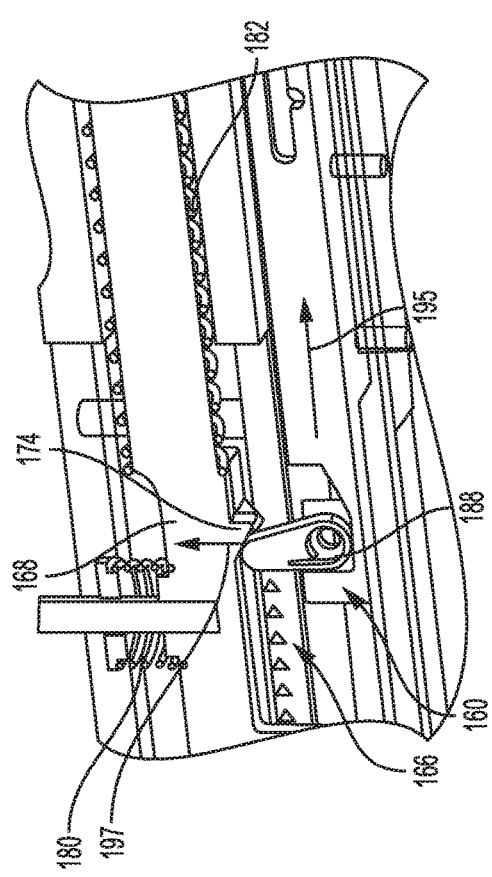
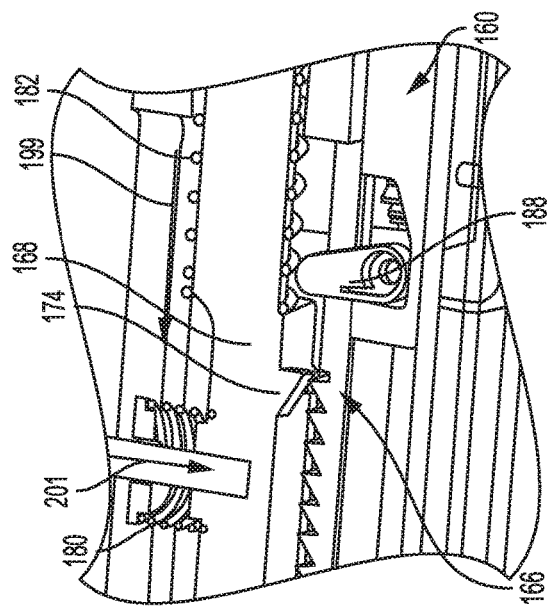
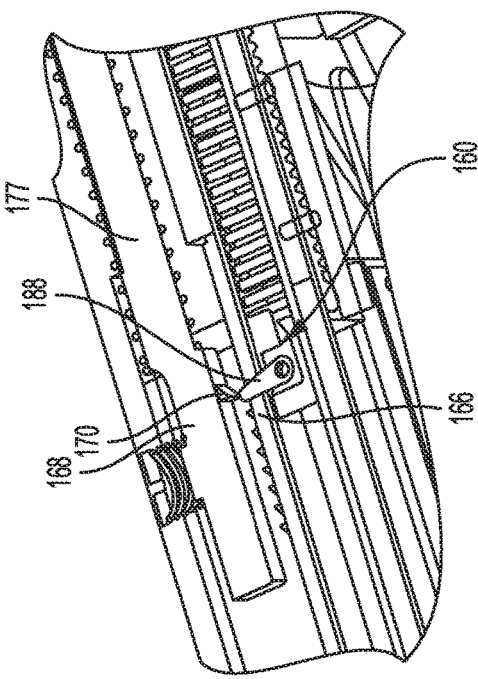
FIG. 17A
FIG. 17B
FIG. 17C

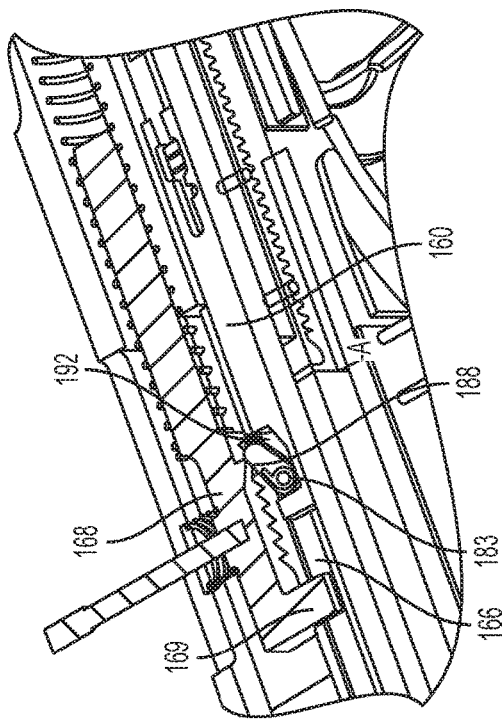
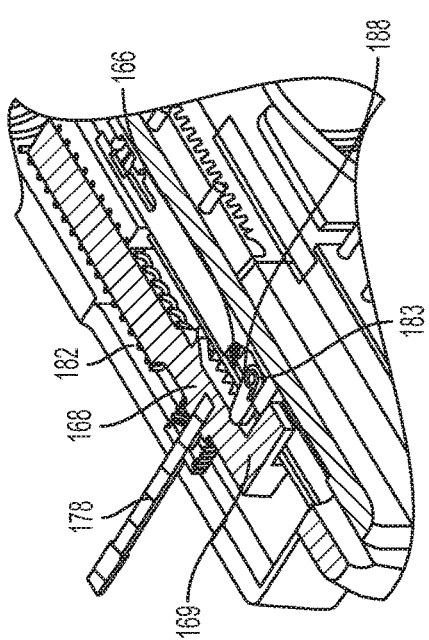
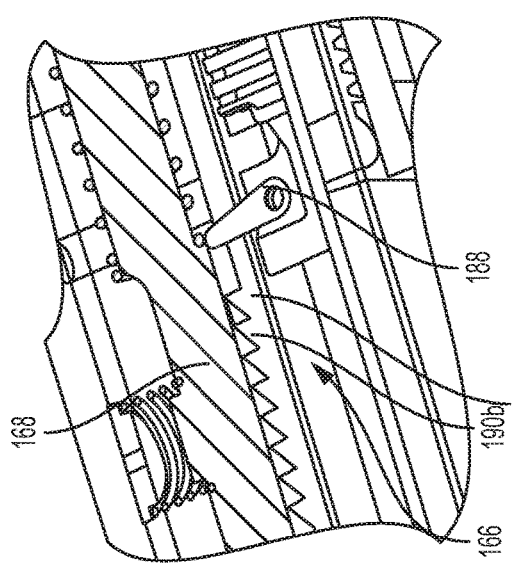
FIG. 17E
FIG. 17F
FIG. 17D

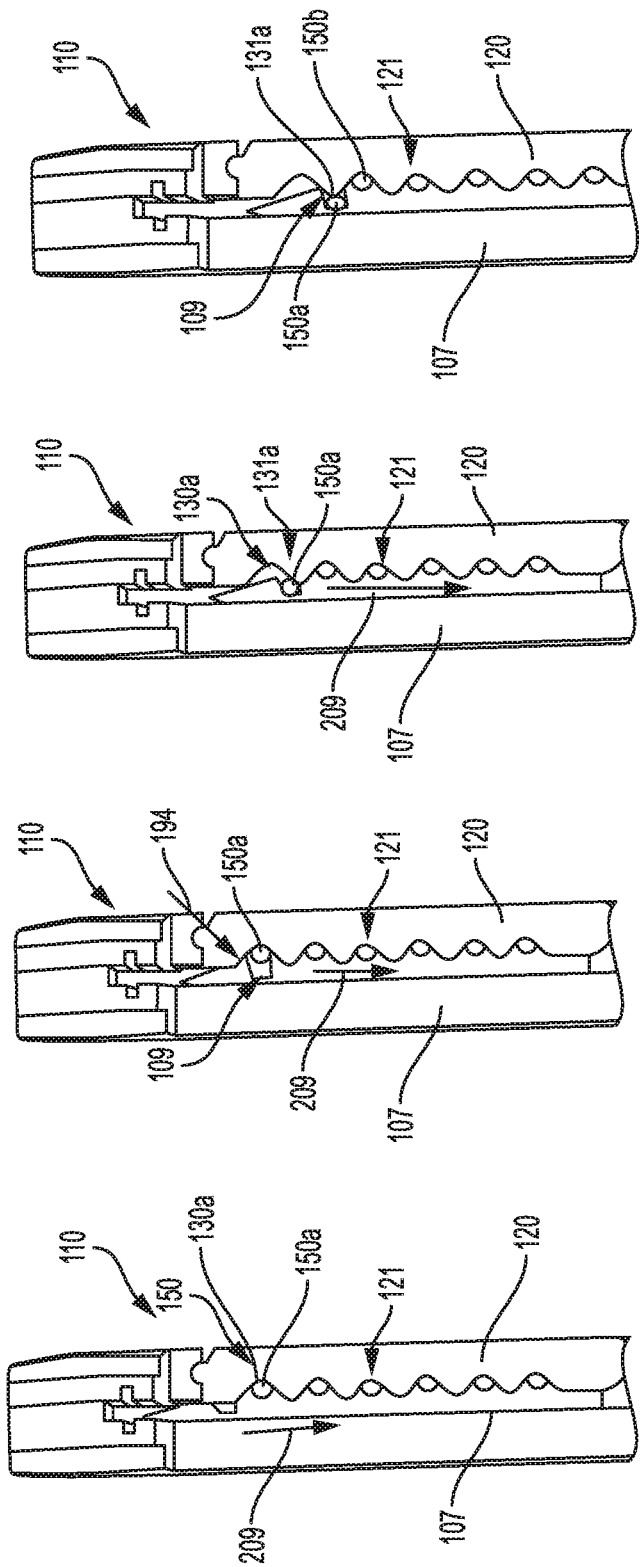

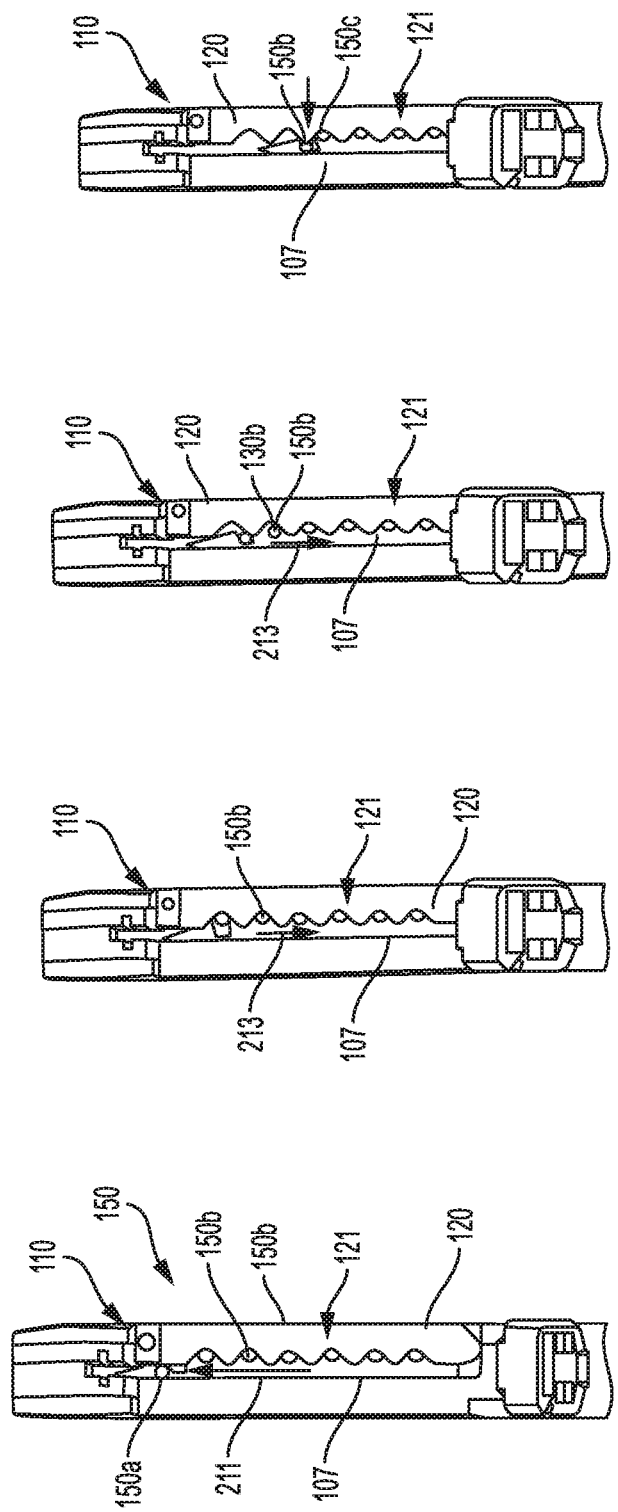

SUTURE MAGAZINE FOR SUTURE PASSING SURGICAL DEVICE

FIELD

The present disclosure relates generally to a suture magazine for a surgical device for suture passing.

BACKGROUND

A variety of injuries and conditions require repair of soft tissue damage, or reattachment of soft tissue to bone and/or surrounding tissue. For example, when otherwise healthy tissue has been torn away from a bone, such as a shoulder rotator cuff tendon being partially or completely torn from a humerus (a rotator cuff tear), surgery is often required to reattach the tissue to the bone, to allow healing and a natural reattachment to occur. A number of devices and methods have been developed for performing these surgical repairs.

Many surgical procedures involve the need to pass a suture through soft tissue. Direct access to the tissue, however, may not be possible, for example, in an arthroscopic procedure. Generally, antegrade or retrograde suture passing techniques are used. An antegrade instrument, having a suture coupled thereto, can be forcibly driven through soft tissue, after which the suture is disengaged from the instrument and the instrument is removed from the surgical site. Antegrade suture passers are commonly used in arthroscopic rotator cuff repair. Retrograde passing involves driving an empty passer through the soft tissue and then manipulating it such that it captures a length of suture already inside the body. The passer is then removed from the soft tissue and pulls the suture through with it. In both antegrade and retrograde suture passing techniques, one of the disadvantages is that it can be quite difficult to disengage the suture from the jaws of the passer. Another drawback is that, after each suture passing, the surgical suture passer needs to be taken out of the patient's body to load a needle of the instrument with the suture for a subsequent passing step.

Accordingly, there remains a need for improved suture passer devices, systems, and methods.

SUMMARY

In general, a surgical instrument for use in passing suture through tissue is provided that includes a suture magazine. In one aspect, a surgical instrument for use in passing suture through tissue is provided that in some embodiments includes first and second jaws disposed on a distal end of an elongate shaft and configured to grasp tissue therebetween, the first jaw having a cavity configured to seat a removable and replaceable suture magazine. The surgical instrument also includes a needle selectively movable along a longitudinal channel extending through an outer side wall of the first jaw and having a suture retaining feature that is formed at a distal end thereof and configured to grasp a suture releasably coupled to the suture magazine.

The surgical instrument can vary in any number of ways. For example, the first jaw can have a retaining feature configured mate with a corresponding retaining feature of the suture magazine. As another example, the retaining feature of the first jaw can be configured to mate with a snap feature. As a further example, the first jaw can have distal and proximal positioning features disposed at distal and proximal ends thereof and configured to mate with corresponding distal and proximal positioning features of the suture magazine to maintain a position of the suture magazine relative to the first jaw.

In some embodiments, the surgical instrument further includes a handle disposed at a proximal end of the elongate shaft, the handle having an actuator configured to selectively activate the needle. In some embodiments, the suture retaining feature of the needle can be a notch.

In some embodiments, the surgical instrument further includes the suture magazine having the retaining feature configured to releasably mate with the retaining feature of the first jaw. The suture magazine has a longitudinal slot configured to facilitate passage of the needle therethrough. The suture magazine can have at least one suture releasably coupled thereto by forming a plurality of suture loops disposed around a side wall of the suture magazine and along a plurality of suture-retaining features spaced apart along a longitudinal axis of the suture magazine. In some embodiments, the suture-retaining features include or are slots formed in the side wall of the suture magazine.

In some embodiments, the surgical instrument further includes a suture magazine carrier removably coupled to the suture magazine. The suture magazine carrier can vary in many ways. For example, the suture magazine carrier can be configured to seat the suture magazine such that the suture loops are formed around the suture magazine.

In some embodiments, a surgical system is provided that includes the surgical instrument for use in passing suture through tissue. The surgical instrument includes first and second jaws disposed on a distal end of an elongate shaft and configured to grasp tissue therebetween, the first jaw having a cavity configured to seat a removable and replaceable suture magazine. The surgical instrument also includes a needle selectively movable along a longitudinal channel extending through an outer side wall of the first jaw and having a suture retaining feature that is formed at a distal end thereof and configured to grasp a suture releasably coupled to the suture magazine. The suture magazine carrier with the suture magazine removably coupled thereto can be coupled to an anchor inserter instrument.

In another aspect, a surgical method is provided that in some embodiments includes positioning first and second jaws of a suture passing surgical instrument such that the first and second jaws grasp tissue within a body of a patient, and sequentially activating the surgical instrument to cause a needle to move along a longitudinal channel extending through one of the jaws such as the needle is advanced distally to pass through the tissue to pass a suture loop coupled to the needle with each activation of the needle. Following each passage through the tissue, the jaws remain in the body, the needle is retracted proximally, and a subsequent suture loop is loaded onto the needle.

The surgical method can vary in many different ways. For example, a first suture loop can be loaded onto the needle prior to positioning the jaws so as to grasp the tissue.

In a further aspect, a suture holding construct is provided that includes a suture magazine. The suture magazine includes a body having a plurality of suture-retaining features spaced along a longitudinal axis of the suture magazine extending between proximal and distal ends of the body, and a plurality of suture loops formed from at least one suture strand, disposed around the body and along the suture-retaining features.

The suture holding construct can vary in any number of ways. For example, the suture-retaining features can be or can include slots. As another example, the suture magazine further includes at least one mating feature configured to releasably mate with a corresponding mating feature of the jaw, and a longitudinal slot extending between the proximal and distal ends and configured to receive a needle of the suture delivery device therethrough. In some embodiments, the at least one mating feature can be or can include an arm extending from a side of the body at the proximal end thereof, the arm having a snap feature.

In some embodiments, the suture holding construct further includes a suture magazine carrier removably attached to the suture magazine. The suture magazine carrier can include a cavity configured to seat therein the suture magazine, and a plurality of suture passing slots, the suture loops being disposed such that each loop extends along a suture-retaining feature and a corresponding slot of the suture passing slots.

BRIEF DESCRIPTION OF DRAWINGS

This disclosure will be more fully understood from the following detailed description taken in conjunction with the accompanying drawings, in which:

FIG. 3 is a top cross-sectional view of the surgical instrument of FIG. 1;

FIG. 5 is a perspective view of one embodiment of a suture magazine;

FIG. 6 is a perspective view of the suture magazine of FIG. 5, showing the suture magazine attached to a suture magazine carrier;

FIG. 10 is a perspective partial view of components of a handle of the surgical instrument of FIG. 1;

FIG. 11 is a top cross-sectional view of components of the handle of the surgical instrument of FIG. 1;

FIG. 16A is a top cross-sectional view of a lower jaw of the surgical instrument of FIG. 1, illustrating a needle advanced into the lower jaw prior to loading a suture to the lower jaw;

FIG. 16B is another top perspective view of the jaws of the surgical instrument of FIG. 1, illustrating a suture magazine attached to a suture magazine carrier being coupled to the lower jaw;

FIG. 16C is another top perspective view of the jaws of FIG. 16B, illustrating the suture magazine carrier being separated from the suture magazine that is coupled to the lower jaw;

FIG. 17A is a top, partially cross-sectional view of components of the handle of the surgical instrument of FIG. 1, illustrating a method of operating the surgical instrument;

FIG. 17B is another top, partially cross-sectional view of the components of the handle of FIG. 17A, illustrating the method of operating the surgical instrument;

FIG. 17C is another top, partially cross-sectional view of the components of the handle of FIG. 17B, illustrating the method of operating the surgical instrument;

FIG. 17D is another top, partially cross-sectional view of the components of the handle of FIG. 17C, illustrating the method of operating the surgical instrument;

FIG. 17E is another top, partially cross-sectional view of the components of the handle of FIG. 17D, illustrating the method of operating the surgical instrument;

FIG. 17F is another top, partially cross-sectional view of the components of the handle of FIG. 17E, illustrating the method of operating the surgical instrument;

FIG. 19A is a top cross-sectional view of one embodiment of a lower jaw of a surgical instrument, illustrating a method of loading a suture to a needle selectively movable along the lower jaw;

FIG. 19B is another top cross-sectional view of the lower jaw of FIG. 19A, illustrating the method of loading the suture to the needle;

FIG. 19C is another top cross-sectional view of the lower jaw of FIG. 19B, illustrating the method of loading the suture to the needle;

FIG. 19D is another top cross-sectional view of the lower jaw of FIG. 19C, illustrating the method of loading the suture to the needle;

FIG. 20A is a top cross-sectional view of a lower jaw of FIG. 19D, illustrating distal advancement of the needle loaded with a first portion of the suture;

FIG. 20B is another top cross-sectional view of the lower jaw of FIG. 20A, illustrating the method of loading the suture to the needle;

FIG. 20C is another top cross-sectional view of the lower jaw of FIG. 20B, illustrating the method of loading the suture to the needle;

FIG. 20D is another top cross-sectional view of the lower jaw of FIG. 20C, illustrating the method of loading the suture to the needle;

DETAILED DESCRIPTION

Figure 1:
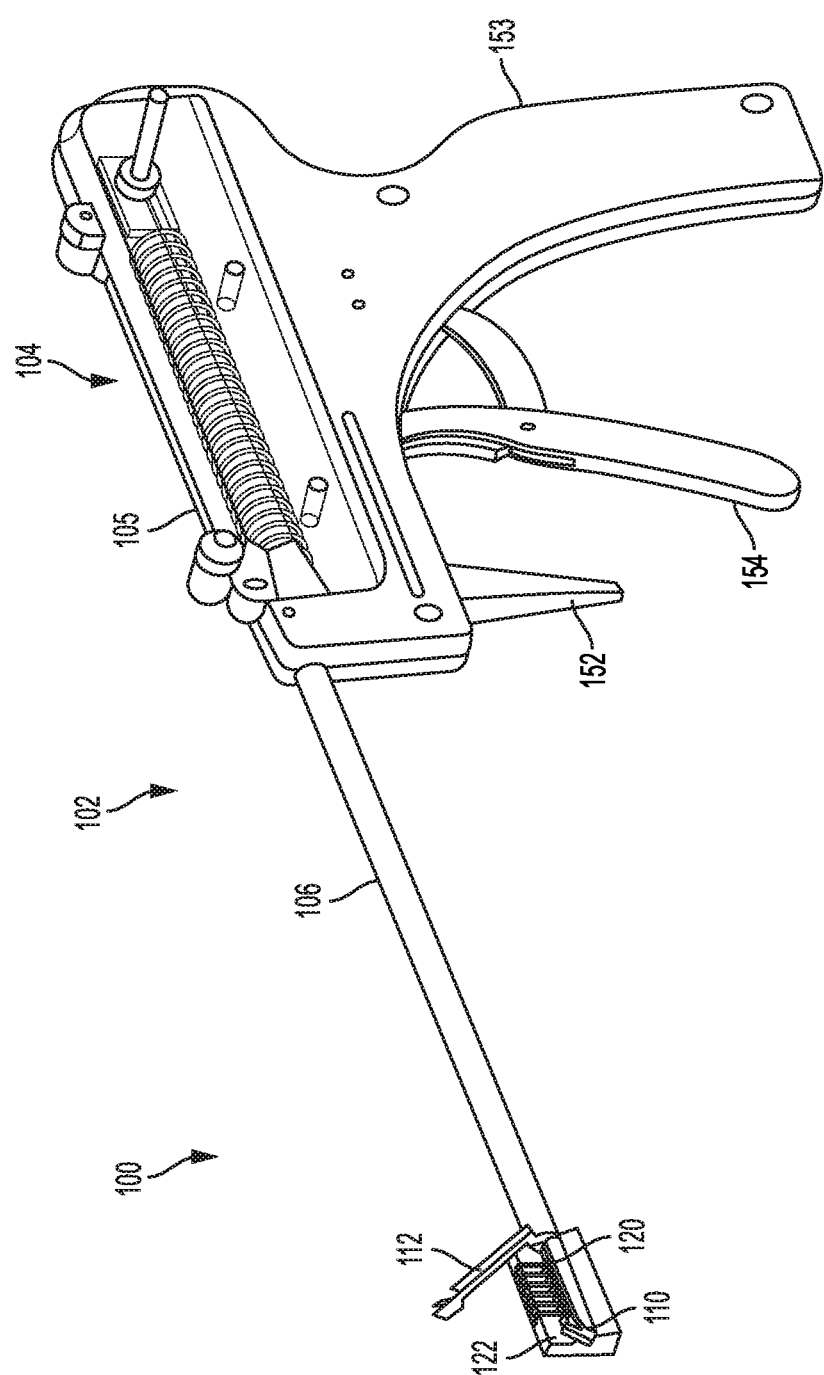
FIG. 1 is a perspective view of one embodiment of a surgical instrument for suture passing having a suture magazine and a suture magazine carrier coupled thereto.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

A suture passing surgical instrument for use in passing suture through tissue is provided. In general, the surgical instrument includes first and second jaws disposed on a distal end of an elongate shaft and configured to grasp tissue therebetween, and a needle selectively movable along a longitudinal channel extending through an outer side wall of the first jaw. In one aspect the jaw has a cavity configured to seat a removable and replaceable suture magazine having a suture releasably coupled thereto, and the needle has a suture retaining feature that is formed at a distal end thereof and configured to grasp the suture coupled to the suture magazine. The surgical instrument described herein is particularly useful in minimally invasive surgical procedures, including arthroscopic surgical procedures.

Prior to use of the suture passing surgical instrument to pass the suture through tissue, the suture magazine can be coupled to a suture magazine carrier. The suture can be coupled to the suture magazine such that the suture is also coupled to the suture magazine carrier. This prevents suture tangling and improves overall suture management. A suture holding construct encompassing the suture magazine and the suture magazine carrier with the suture coupled thereto is coupled to first jaw of the surgical instrument, and the suture magazine carrier is then separated from the suture magazine such that the suture remains with the suture magazine. In some embodiments, the suture holding construct can be removably coupled to a suture anchor inserter configured to insert into bone a suture anchor that is coupled to a suture, with the suture also being coupled to the suture holding construct.

In use, the suture magazine coupled to the surgical instrument's jaw enables the loading of portions (e.g., loops) of the suture to the suture passing needle while the jaws remain in the patient's body. In particular, following each passage of the needle with through tissue, the needle is retracted proximally such that a subsequent suture loop is loaded onto the needle as the needle is being retracted proximally. The needle with the subsequent suture loop loaded thereto is passed through the tissue upon the next activation of the surgical instrument to advance the needle distally. The jaws remain in the patient's body throughout the multiple steps of passing of the suture through the tissue. Accordingly, once the suture magazine is coupled to the jaw (e.g., a lower jaw) of the surgical instrument, loading portions of the suture to a suture passing needle of the surgical instrument is done automatically as the needle is retracted proximally after its distal advancement. This avoids the need to remove the surgical instrument from the patient's body to load the suture thereto once the surgical instrument is passed to a surgical site in the patient's body. The described techniques thus allow performing a surgical procedure for passing suture through tissue in a more time- and cost-saving manner. In addition, because the surgical procedure is simplified, the possibility of a surgical error is decreased or eliminated.

Figure 2:
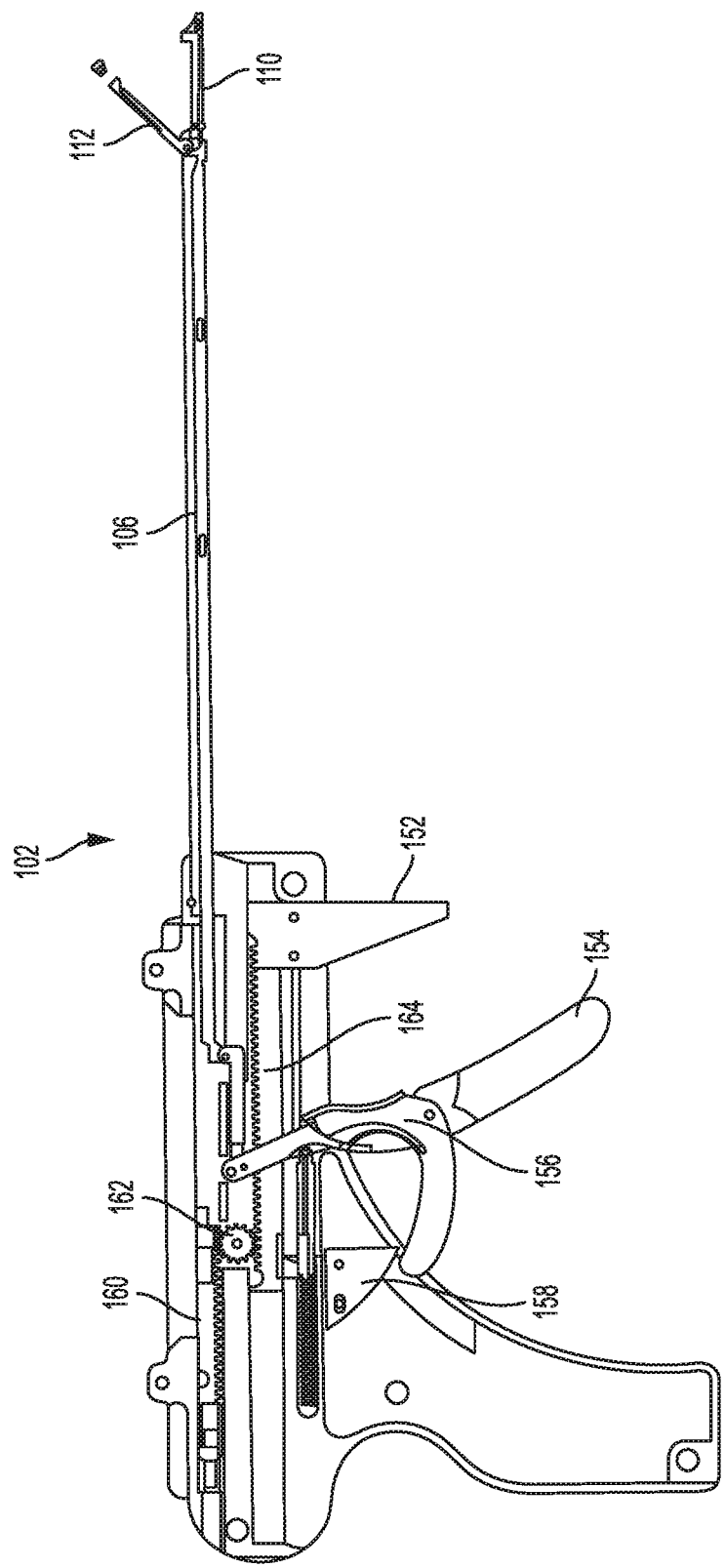
FIG. 2 is a side cross-sectional view of the surgical instrument of FIG. 1, without a suture magazine carrier.

FIGS. 1-3 illustrate one embodiment of a surgical system 100 including a surgical instrument 102, also referred to as a suture delivery device, for use in passing suture through tissue that includes a proximal handle 104, an elongate shaft 106 extending distally from the handle 104, and first and second jaws 110, 112 disposed on a distal end 106d of the elongate shaft 106. In the illustrated embodiment, the first and second jaws 110, 112 are lower and upper jaws, respectively, that are configured to grasp tissue therebetween. The surgical instrument 102 also has a needle 107 configured to be selectively activated. The needle 107 can retain a suture and pass the suture through tissue, as discussed in more detail below.

A housing 105 of the proximal handle 104 has an actuator 152, such as a firing trigger that is configured to selectively activate a needle. The needle can be activated to be distally advanced, as discussed in more detail below. The housing 105 also has a stationary handle 153 and a jaw approximation trigger 154 configured to be activated to approximate the lower and upper jaws 110, 112 to thereby cause the jaws 110, 112 to clamp therebetween tissue to be treated. The housing 105 can further have a tissue release trigger 156, shown in FIG. 2, that is activated to release a mechanism retaining the jaws 110, 112 in an approximated position. As also shown in FIG. 2, the housing 105 includes a tissue grasper ratchet 158 configured to lock position of a tissue grasping jaw (e.g., the second jaw 112) when the trigger 154 is actuated. A needle carrier or holder 160 is configured to seat the needle 107 in at least a portion thereof. As shown in FIG. 2, the needle holder 160 is coupled to an actuator 152 of the proximal handle 104 via a circular gear 162 and a gear rack 164. Components of the proximal handle 104 are described in more detail below.

Figure 7:
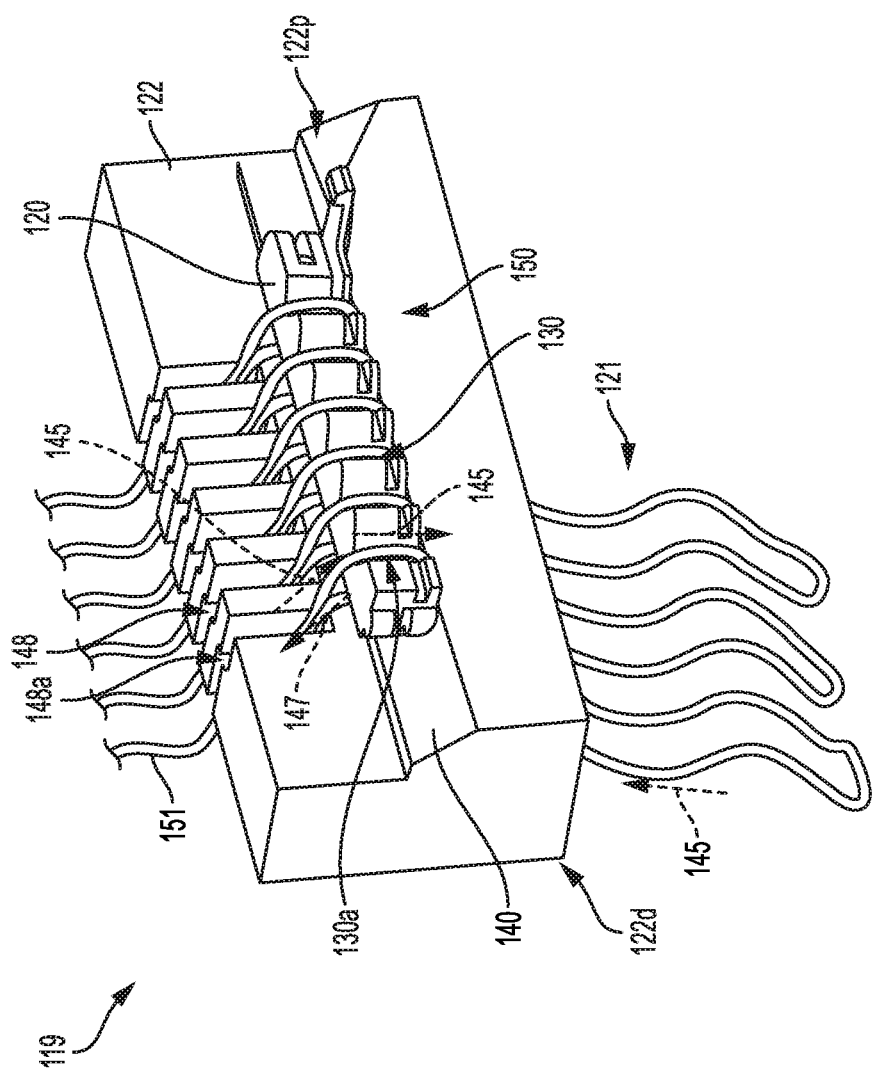
FIG. 7 is a perspective view of the suture magazine and the suture magazine carrier of FIG. 6, showing a suture coupled thereto.

In the illustrated embodiment, as shown in FIG. 1, the surgical instrument 102 has a removable and replaceable suture magazine 120 attached to the lower jaw 110. Although not shown in FIG. 1, the suture magazine 120 has a suture 121 releasably coupled thereto, as shown in FIG. 7. The suture 121 is loaded onto the needle 107 from the suture magazine 120, as discussed in more detail below. The suture magazine 120 can be removably coupled to a suture magazine carrier 122, which is shown coupled to the suture magazine 120 in FIG. 1 and also shown in FIGS. 6 and 7, which is separated from the suture magazine 120 prior to activation of the surgical instrument 102. The suture magazine 120 and the suture magazine carrier 122 are discussed in more detail below.

Figure 4A:
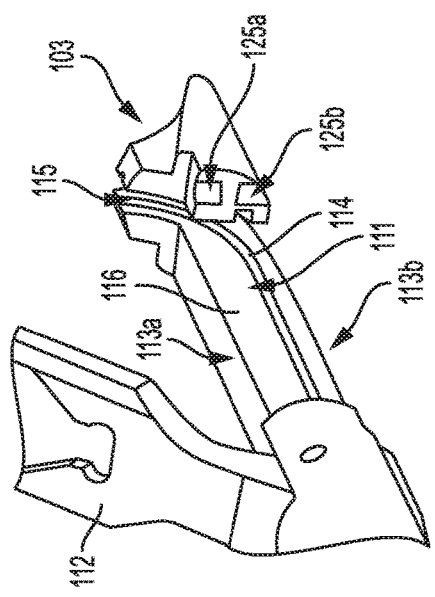
FIG. 4A is a perspective view of jaws of the surgical instrument of FIG. 1.
Figure 4C:
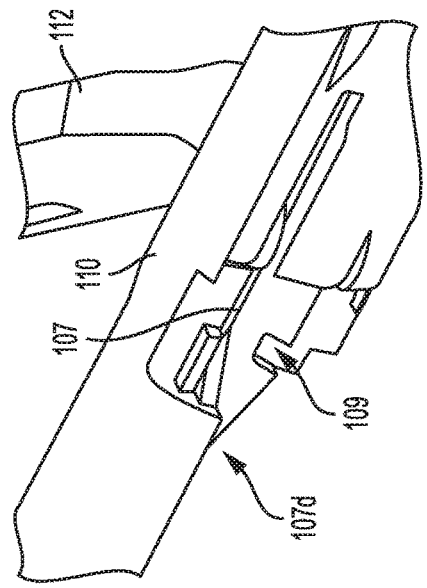
FIG. 4C is another perspective view of the jaws of the surgical instrument of FIG. 1.
Figure 8A:
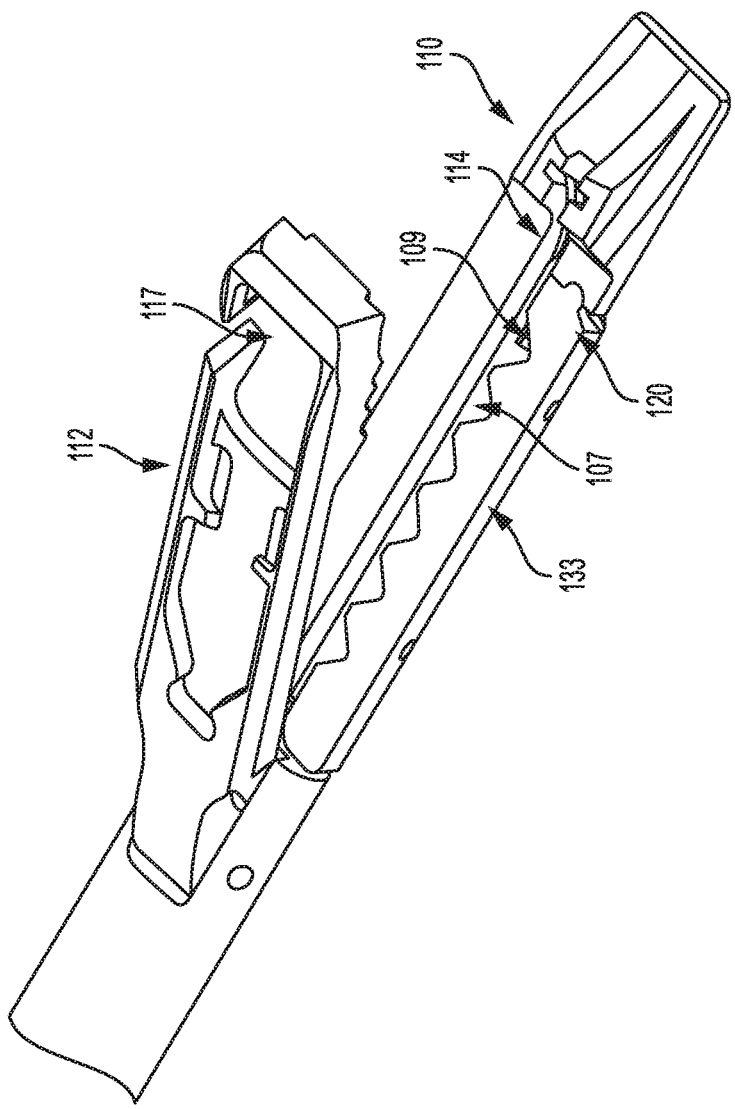
FIG. 8A is a perspective view of the jaws of the surgical instrument of FIG. 1, showing a lower jaw with the suture magazine coupled thereto.

The lower and upper jaws 110, 112 can have various configurations. As shown in FIGS. 4A-4D, the lower jaw 110, has a distal tip 103 and a longitudinal channel 114 extending through an outer side wall 116 of the lower jaw 110, between proximal and distal ends 110p, 110d of the jaw 110. As shown, the longitudinal channel 114 extends such that it is closer to a bottom surface 113b of the jaw 110, which is the surface opposite to lower jaw's tissue contacting surface 113a that faces the upper jaw 112. The longitudinal channel 114 of the lower jaw 110 is configured to receive and guide the needle 107 therethrough, as shown in FIGS. 4C and 4D. As shown in FIG. 4A, the longitudinal channel 114 extends through the distal tip 103 in the form of a keying feature 115 and curves upward, towards the upper jaw 112, as also shown in FIG. 8A and further discussed below. Such a configuration allows the needle to be guided through the channel 114 and the keying feature 115 of the channel 114 such that the needle extends distally from the channel and into tissue, as discussed below.

In the illustrated embodiments, the lower jaw 110 can also have features that facilitate positioning and removable attachment of the suture magazine 120 thereto. Such features allow for a straightforward coupling of the suture magazine to the lower jaw 110 prior to a surgical procedure. For example, the suture magazine 120 can be guided by the features to "snap" into place.

Accordingly, as shown in FIG. 4A, the lower jaw 110 has a cavity 111 configured to seat the removable and replaceable suture magazine 120. The lower jaw 110 can also have a retaining feature 118, shown in FIG. 4D, that is configured to mate with a corresponding retaining feature of the suture magazine 120. The retaining feature 118 is disposed at the proximal end 110p of the lower jaw 110, as additionally shown in FIG. 4D. In this example, the retaining feature 118 can be in the form of a protrusion configured to mate with a corresponding (e.g., complementary) feature of the suture magazine as discussed in more detail below. The protrusion 118 can be a generally rectangular protrusion, though it can have any other configuration. The lower jaw 110 can have one or more retaining features of any suitable type, including feature(s) that can be formed on the distal end of the lower jaw. Regardless of their configuration, the one or more retaining features are configured to releasably retain corresponding feature(s) of the suture magazine.

Figure 4B:
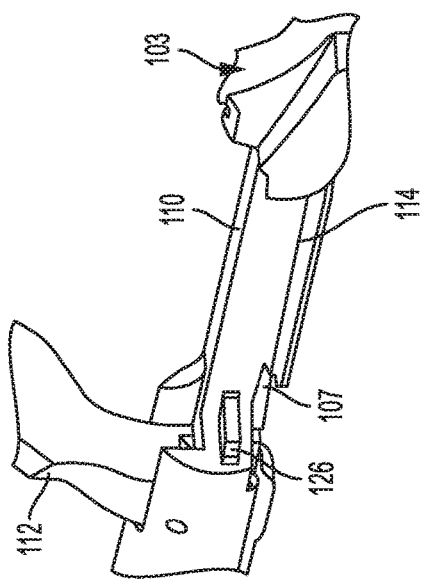
FIG. 4B is another perspective view of the jaws of the surgical instrument of FIG. 1.
Figure 4D:
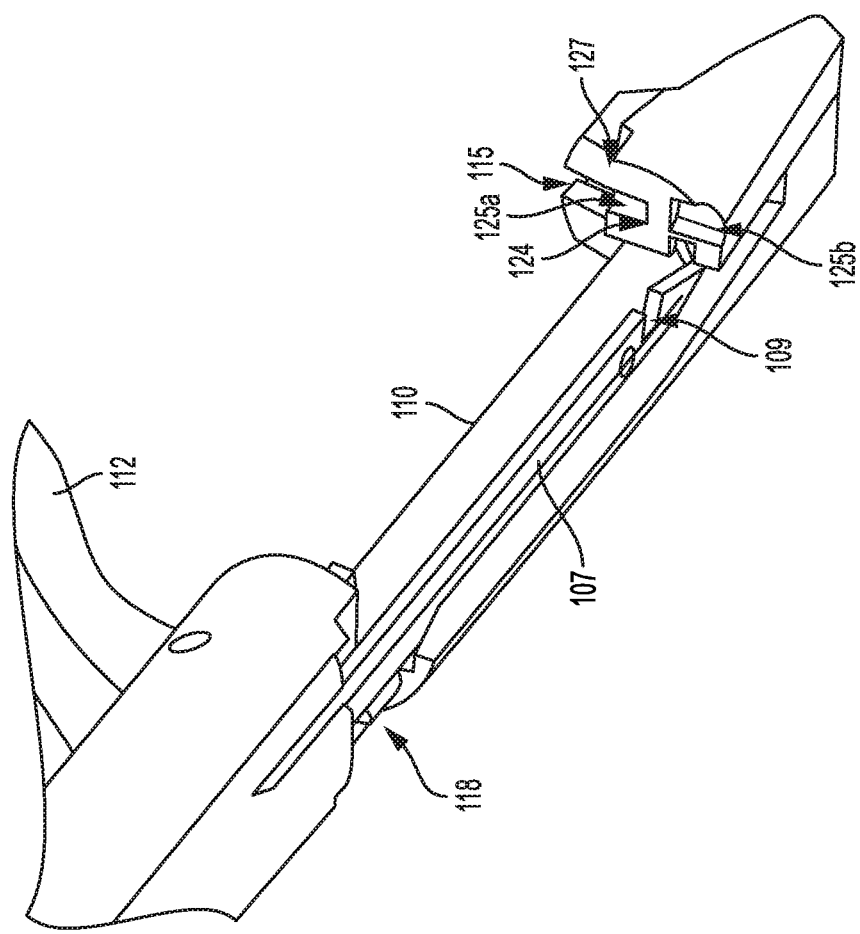
FIG. 4D is a further perspective view of the jaws of the surgical instrument of FIG. 1.

As shown in FIGS. 4A, 4B, and 4D, the lower jaw 110 can also have distal and proximal positioning features 124, 126 disposed at the distal and proximal ends 110d, 110p thereof and configured to mate with corresponding distal and proximal positioning features of the suture magazine 120 to facilitate alignment and maintain the position of the suture magazine 120 relative to the lower jaw 110. In the illustrated embodiment, the distal positioning feature 124 is in the form of first (upper) and second (lower) recesses 125a, 125b formed in a proximal-facing wall 127 at the distal end 110d of the lower jaw 110. The proximal positioning feature 126 is in the form of a protrusion, shown in FIG. 4B, that is configured to mate with a corresponding recess (e.g., a complementary recess) in the suture magazine 120. In some embodiments, the lower jaw can have only one of the distal and proximal positioning features. Furthermore, it should be appreciated that the lower jaw 110 can have any number of positioning features of any suitable type that can be formed at any location on the lower jaw and configured to mate with corresponding positioning features of a suture magazine. In addition, in some implementations, the lower jaw may have no positioning features.

The needle 107 is selectively movable along the longitudinal channel 114 of the lower jaw and it is configured to grasp the suture 121 releasably coupled to the suture magazine 120. The needle 107 can have various configurations. In the illustrated embodiment, the needle 107 is a flexible needle that has a suture retaining feature 109 formed at its distal end 107d. The suture retaining feature 109 can be a notch (indentation) or a feature of another type configured to releasably retain a portion of a suture when the suture is loaded onto the needle 107.

As mentioned above, in the described embodiment, the surgical instrument 102 can have the suture magazine 120 removably coupled thereto. The suture magazine 120 can retain the suture 121 that can be in the form of a plurality of suture loops. The suture magazine 120 can be coupled to a jaw of the surgical device 102, such as the lower jaw 110. The needle 107 can sequentially grasp portions of the suture 121 (e.g., loops) from the suture magazine 120 and pass the suture through tissue at a surgical side in the patient's body while the jaws 110, 112 of the surgical instrument 102 remain in the body.

The suture magazine 120 can have a variety of configurations. In the illustrated embodiments, as shown in FIGS. 5-7, the suture magazine 120 has a body 128 having a plurality of suture-retaining features 130 spaced apart along a longitudinal axis A of the suture magazine 120 extending between proximal and distal ends 128p, 128d of the body. As shown in FIGS. 5-7, the suture-retaining features 130 can be in the form of pockets or slots formed in a side wall 132 of the suture magazine 120. In this example, six triangular-shaped suture-retaining slots 130 are formed, two of which are marked in FIG. 5. However, it should be appreciated that other number of suture-retaining slots (e.g., less than six or greater than six), or other features of any suitable configuration, can be used for retaining a suture. Regardless of their number and design, the suture-retaining features are configured to seat portions (e.g., loops) of a suture therethrough, so as to facilitate loading of a suture onto a needle of a surgical instrument.

As shown in FIGS. 5 and 6, in the illustrated example, the suture-retaining features 130 are formed in the side wall 132 of the suture magazine 120 such that protrusions 131 are formed in the side wall 132 between the slots 130. The protrusions 131 assist in loading a suture coupled to the suture magazine 120 onto the needle 107, as discussed below.

Figure 8B:
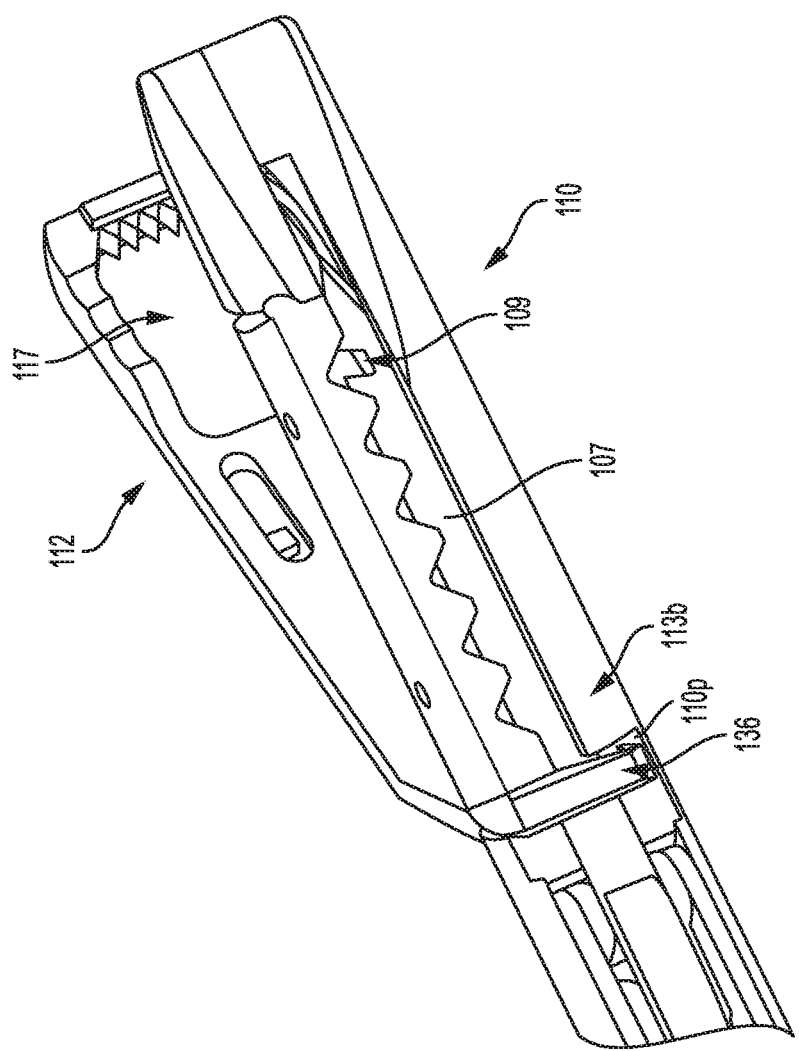
FIG. 8B is another perspective view of the jaws of FIG. 8A.

As also shown in FIGS. 5 and 6, the suture magazine 120 has a longitudinal slot 134 extending between the proximal and distal ends 128p, 128d of the body 128 along the side wall 132. The longitudinal slot 134 is configured to receive the needle 107 of the surgical instrument 102 therethrough. In particular, when the suture magazine 120 is coupled to the lower jaw 110 of the surgical instrument 102, the needle 107 movably extends through the longitudinal channel 114 of the lower jaw 110 such that the needle 107 is at least partially disposed within the longitudinal slot 134 of the suture magazine 120, as shown in FIGS. 8A and 8B. The needle 107 extends through the longitudinal slot 134 such that the suture retaining feature 109 of the needle 107 faces the longitudinal channel 114 of the lower jaw 110. In this way, as the needle 107 is retracted proximally following its activation, a suture loop of the suture 121 coupled to the suture magazine 120 is loaded onto the needle 107, as discussed in more detail below. The upper jaw 112 has a cut out 117 at a distal portion thereof, through which a suture can pass when the suture is decoupled from the jaws.

The suture magazine 120 has other features that facilitate positioning and retention of the suture magazine 120 on the lower jaw 110 of the surgical instrument 102. As discussed above, the lower jaw 110 can have the retaining feature 118 configured to mate with a corresponding (e.g., complementary) retaining feature of the suture magazine 120. As in the described embodiments, the corresponding retaining or mating feature of the suture magazine 120 can be, for example, an arm 136 with the protrusion or snap feature 138. As shown in FIGS. 5 and 6, the arm 136 extends from a side of the suture magazine's body 128 at the proximal end 128p thereof. When the suture magazine 120 is coupled to the lower jaw 110, the arm 136 is disposed over the bottom surface 113b of the lower jaw 110 such that the snap feature 138 mates with the retaining feature 118 of the lower jaw 110, as shown in FIG. 8B. It should be appreciated that the snap feature 138 and the corresponding retaining feature 118 can have any other suitable configurations.

In the example illustrated, the suture magazine 120 also has distal and proximal positioning features 144, 146 configured to mate with the corresponding distal and proximal positioning features 124, 126 of the lower jaw 110. The distal and proximal positioning features 144, 146 are formed on end side walls at the distal and proximal ends 128d, 128p of the body 128 of the suture magazine 120, respectively. As shown in FIGS. 5 and 6, the distal positioning feature 144 of the suture magazine 120 is in the form of protrusions 135a, 135b configured to mate with the first and second recesses 125a, 125b of the lower jaw 110. In this example, the protrusions 135a, 135b are semi-cylindrical members stacked along an axis perpendicular to the longitudinal axis A of the suture magazine 120. The proximal positioning feature 146 of the suture magazine 120 is in the form of a recess configured to mate with the corresponding proximal positioning feature 126 of the lower jaw 110 that is in the form of a protrusion. It should be appreciated that the distal and proximal positioning features 144, 146 of the suture magazine 120, as well as the corresponding distal and proximal positioning features 124, 126 of the lower jaw 110, can have any other suitable configurations. As another variation, as mentioned above, other types of positioning features can be formed on the suture magazine and the jaw.

As mentioned above, the suture magazine 120 can be removably attached to the suture magazine carrier 122. FIGS. 6 and 7 illustrate an example of a suture holding construct 119 encompassing the suture magazine carrier 122 with the suture magazine 120 removably attached thereto. The suture magazine carrier 122 can have various configurations. In the illustrated embodiments, as shown in FIGS. 1, 6, and 7, the suture magazine carrier 122 is a member having a generally rectangular cross-section along longitudinal lengths thereof. The suture magazine carrier 122 has a cavity 140 configured to seat therein the suture magazine 120. As shown in FIGS. 6 and 7, the cavity 140 extends through a side wall 142 of the suture magazine carrier 122 between proximal and distal ends 122p, 122d of the suture magazine carrier 122. The cavity 140 is sized and shaped to seat a side wall 133 (shown in FIG. 8A) of the suture magazine 120 that is opposite to the side wall 132 in which the suture-retaining features 130 are formed. The suture magazine 120 can be press-fit, snapped, or otherwise mated with the cavity 140 of the suture magazine carrier 122.

The removable coupling of suture magazine carrier 122 to the suture magazine 120 facilitates coupling of one or more sutures to the suture magazine 120 in a manner that prevents suture tangling. A suture can form multiple suture loops around the suture magazine 120. In this way, after the suture magazine 120 with the suture magazine carrier 122 coupled thereto is attached to a jaw of a surgical instrument for passing suture (e.g., the lower jaw 110 of the surgical instrument 102), and the suture magazine carrier 122 is separated from the suture magazine 120 (the suture remains with the suture magazine 120), the suture loops disposed around the suture magazine 120 are ready to be loaded onto the suture passing needle of the surgical instrument.

Figure 9B:
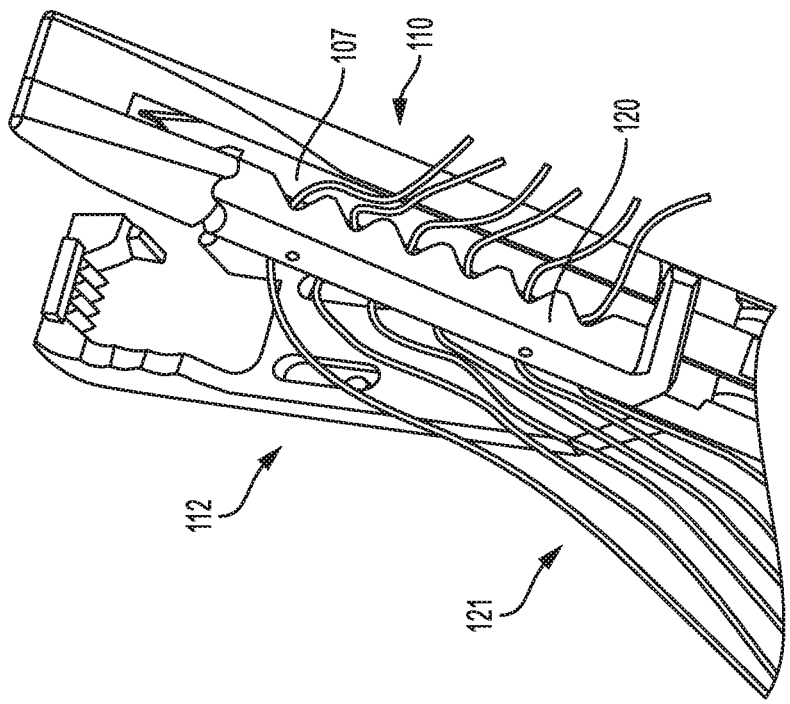
FIG. 9B is another perspective view of the jaws of FIG. 9A.
Figure 9A:
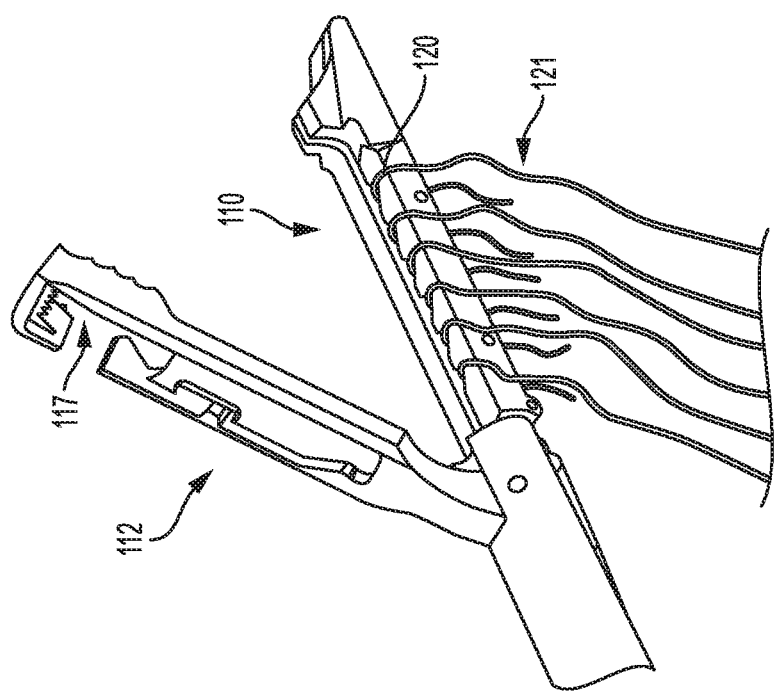
FIG. 9A is a perspective view of the jaws of the surgical instrument of FIG. 1, showing a lower jaw with the suture magazine coupled thereto.

In the illustrated embodiments, as shown in FIG. 7 and additionally in FIGS. 9A and 9B, the suture magazine 120 has the suture 121 releasably coupled thereto. The suture 121 can be in the form of a plurality of suture loops 150 formed from at least one suture strand, disposed around the body 128 and along the suture-retaining features 130 (e.g., slots) of the suture magazine 120. As shown in FIGS. 6 and 7, the suture magazine carrier 122 has a plurality of suture passing slots 148 formed above the cavity 140, two of which are marked. The suture passing slots 148 are spaced along the longitudinal axis A1 of the suture magazine carrier 122 and extend from a top surface 143 of the suture magazine carrier 122 and laterally through the entire thickness of the suture magazine carrier 122, with the top surface 143 being "top" with reference to the suture magazine carrier 122 as shown in FIGS. 6 and 7. In the illustrated example, each of the suture passing slots 148 of the suture magazine carrier 122 has a bend 149 (one of which is marked in FIG. 6), which facilitates suture retention by the suture magazine carrier 122. However, it should be appreciated that the suture passing slots 148 can be straight, or they can have any other configuration.

The suture passing slots 148 are formed such that they are aligned with the suture-retaining features 130 of the suture magazine 120. In this way, as shown in FIG. 7, the suture loops 150 are disposed such that a loop-forming portion extends along one of the suture-retaining features 130 of the suture magazine 120 and along a corresponding slot of the suture passing slots 148 of the suture magazine carrier 122. This facilitates suture retention by the suture magazine 120 and the suture magazine carrier 122 in a manner that prevents suture tangling. Furthermore, the suture magazine carrier 122 is configured such that the suture coupled thereto can be easily separated therefrom when the suture magazine carrier 122 is separated from the suture magazine 120. For example, as shown by arrows 145 in FIG. 7, a suture loop can be formed by passing a portion of the suture 121 in a first direction through a slot 148a of the slots 148 of the carrier 122 towards the suture magazine 120, along a corresponding slot 130a of the magazine's slots 130, around a side of the suture magazine 120, and back (arrow 147) in a second, opposite direction along the side wall 133 of the suture magazine 120 and through the slot 148a such that a suture end 151 extends from the suture magazine carrier 122. It should be appreciated that this way of coupling the suture to the suture magazine 120 and the suture magazine carrier 122 is shown by way of example only. For example, although the suture end 151 is shown in FIG. 7 as a free end, in some embodiments, because one suture strand can be used to form multiple loops around the suture magazine 120, the suture may not terminate after the first loop is formed. Also, one or more of the portions of the suture 121 shown in FIG. 7 below the suture magazine carrier 122 can be a free suture end.

Referring back to FIG. 1, in use, the suture magazine 120 having the suture magazine carrier 122 removably attached thereto is loaded into the lower jaw 110 of the surgical instrument 102. The suture magazine 120 and the suture magazine carrier 122 are shown in FIG. 1, as well as in FIGS. 8A, and 8B, without a suture, for illustration purposes only, and it should be appreciated that the suture magazine 120, attached to the suture magazine carrier 122, is coupled to the lower jaw 110 with suture loops, such as the loops 150 of the suture 121 in FIG. 7, coupled thereto. After the suture magazine 120 is coupled to the lower jaw 110, which can be effected using various retaining and positioning features described above, the suture magazine carrier 122 is separated from the suture magazine 120 such that the suture 121 remains coupled to the suture magazine 120. As a result, the lower jaw 110 has the suture magazine 120 with the suture 121 (e.g., in the form of suture loops 150) coupled thereto, as shown by way of example in FIGS. 9A and 9B illustrating portions of the suture 121.

In the illustrated example, as shown in FIGS. 7, 9A, and 9B, the suture 121 forms six loops 150 such that each of the loops is seated along a corresponding one of the suture-retaining features 130 of the suture magazine 120. In other embodiments, however, the suture magazine can have any other number of suture-retaining features and the suture can form a corresponding different number of suture loops. The suture 121 can include any suitable number of suture strands. For example, in at least some embodiments, the suture 121 can include three suture strands each forming two loops. In other embodiments, different other number of suture strands can be used that can form any suitable number of loops. For example, six different strands each forming one loop can be used. For another example, one suture strand forming six loops can be coupled to the suture magazine (and the suture magazine carrier prior to separation of the carrier from the suture magazine).

FIGS. 10 to 14 illustrate one embodiment of components of the housing 105 of the handle 104 of the surgical instrument 102. As shown, the housing 105 includes a rack 166 and a sequencer 168 that is configured to engage with the rack 166 to set a position of the suture passing needle 107. The sequencer 168 is configured to interact with a needle holder 160 to advance the needle holder 160, and thus the needle 107 coupled to the needle holder 160, distally.

The sequencer 168 can have various configurations. As shown, for example, in FIGS. 11 and 13, it is a generally elongate member extending along a longitudinal axis of the housing 105 and having one a side thereof facing the rack 166. In the illustrated embodiment, the at least one mating feature of the sequencer 168 is in the form of teeth 170 configured to engage with teeth 172 of the rack 166. The sequencer 168 also has a stop surface 169 at a proximal end 168p thereof. The stop surface 169 is configured to prevent proximal movement of the needle holder 160, and a position of the stop surface 169 changes as the sequencer 168 moves to a next position, as discussed below.

Figure 14:
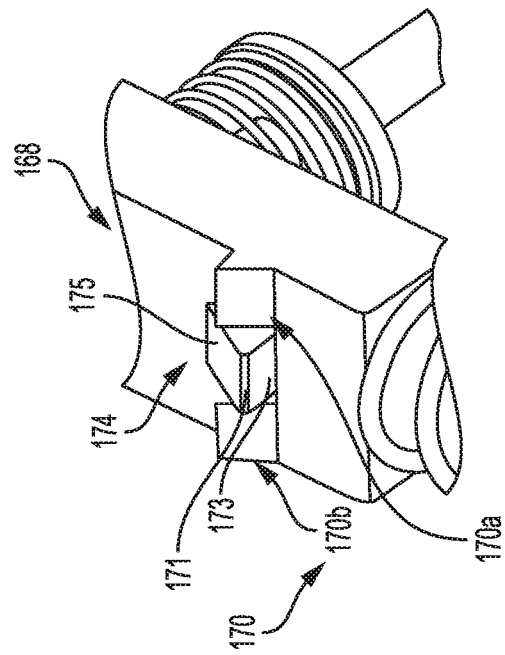
FIG. 14 is a perspective partial view of the sequencer of the surgical instrument of FIG. 1.

In the illustrated embodiment, as shown in FIG. 14, the teeth 170 of the sequencer 168 are in the form of upper and lower teeth 170a, 170b. As also shown in FIG. 14, the sequencer 168 has a ramp feature 174 disposed between the teeth 170a, 170b. In this example, the ramp feature 174 is in the form of a tooth having a top edge 171 and first and second sides 173, 175 extending at opposed sides from the top edge 171. The ramp feature 174 is angled in a direction that is opposite from a direction in which the upper and lower teeth 170a, 170b are angled. The longer second side 175 of the ramp feature 174 defines a trip ramp surface that is discussed below. The teeth 170 of the sequencer 168 can engage the rack's teeth 172 at various positions such that the sequencer 168 can be disposed at different positions with respect to the rack 166.

Figure 12:
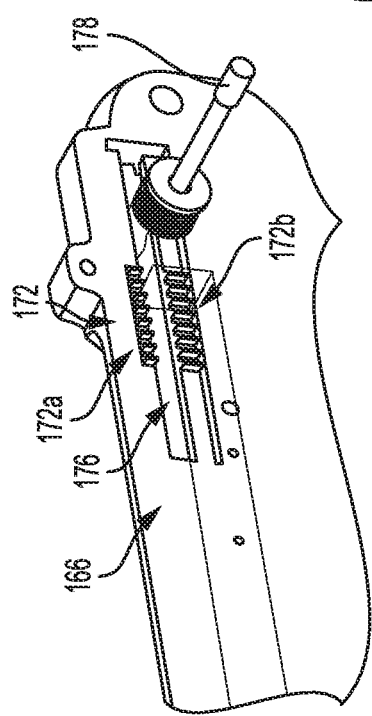
FIG. 12 is a perspective view of a rack of the surgical instrument of FIG. 1.

The rack 166 can have various configurations. In the illustrated embodiment, as shown in FIG. 12, the teeth 172 of the rack 166 can be in the form of two sets of teeth, such as upper and lower teeth 172a, 172b, disposed on opposed sides of a slot 176. In this example, eight pairs of the teeth 172 are formed on the rack 166, though it should be appreciated that the rack 166 can include any other suitable number of teeth. In use, the sequencer 168 is engaged with the rack 166 at different positions with respect to the rack 166 such that sequencer teeth 170a, 170b are engaged with at least one pair of the rack teeth 172. The ramp feature 174 of the sequencer 168 is positioned in the slot 176 of the rack 166.

Figure 13:
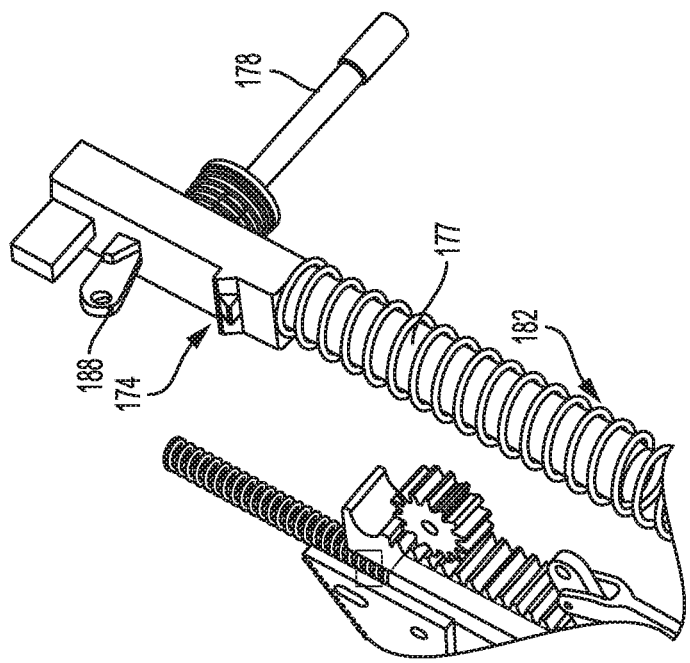
FIG. 13 is a perspective partial view of components of the handle of the surgical instrument of FIG. 1, illustrating a sequencer of the surgical instrument of FIG. 1.

As shown in FIG. 10, the sequencer 168 has a handle 178 configured to set a position of the sequencer 168 before loading a suture magazine onto the surgical instrument 102. A first spring 180 coupled to the handle 178 and biases the sequencer 168 and the rack's teeth 172a, 172b inward (i.e., towards the inside of the housing 105). The handle 178 can be, for example, a cocking handle configured to be moved to a retracted position (away from the housing 105) and, as it is maintained in its retracted position, it can be moved proximally to a desired position to thereby set a position of the sequencer 168. The housing 105 also includes a second spring 182 (e.g., a compression spring) that is disposed over a tubular shaft 177 extending distally from the sequencer 168 and that is configured to bias the sequencer 168 into engagement with the rack 166. In this way, the second spring 182 assists in moving the sequencer 168 to a next position with respect to the rack 166 after the sequencer 168 is disengaged from the rack 166, as discussed below. The tubular shaft 177 having the second spring 182 coupled thereto as shown in FIGS. 10, 11, and 13 and in other figures, can be formed integrally and/or monolithically with the sequencer 168, and can thus be part of the sequencer 168.

The needle carrier 160 coupled to the needle 107 can have various configurations. In the illustrated embodiment, the needle carrier 160 has a body 184 having an arm feature 186 at one end thereof. As shown in FIG. 11, the arm feature 186 has a flip-flop or toggle 188 pivotally coupled thereto. The toggle 188 is configured to engage (e.g., frictionally) with the sequencer 168, as discussed in more detail below.

Figure 15A:
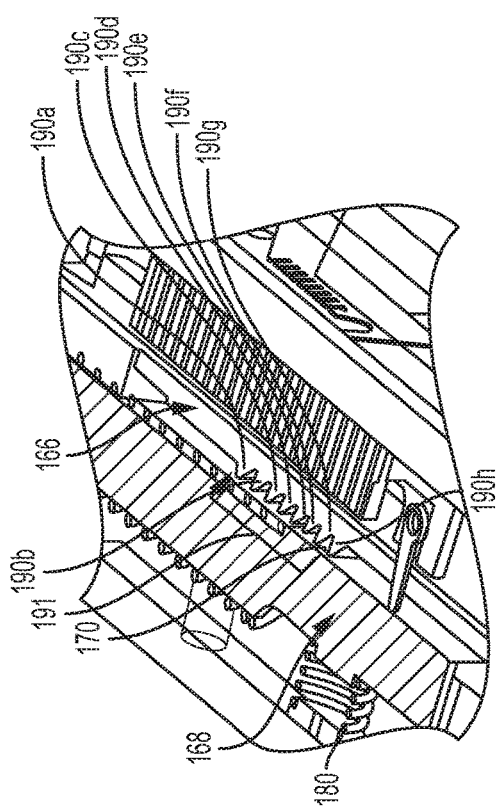
FIG. 15A is a top cross-sectional view of components of the handle of the surgical instrument of FIG. 1, illustrating a method of operating the surgical instrument.

As shown in FIG. 15A, in the original configuration of the device 102, prior to its activation, the teeth 170 of the sequencer 168 are engaged between a proximal-most pair of teeth 190h and a pair of teeth 190g adjacent to the teeth 190h of the teeth 172 of the rack 166. One of the teeth 170 of the sequencer 168, such as the upper tooth 170a, is visible in FIG. 15A and the lower tooth 170b is obscured. Similarly, only a row of the upper teeth 172a of the rack's teeth 172 is visible in FIG. 15A. As also shown in FIG. 15A, in the original configuration, the toggle 188 of the needle holder 160 is disposed proximal to the proximal-most pair of teeth 190h of the rack's teeth 172.

Figure 15C:
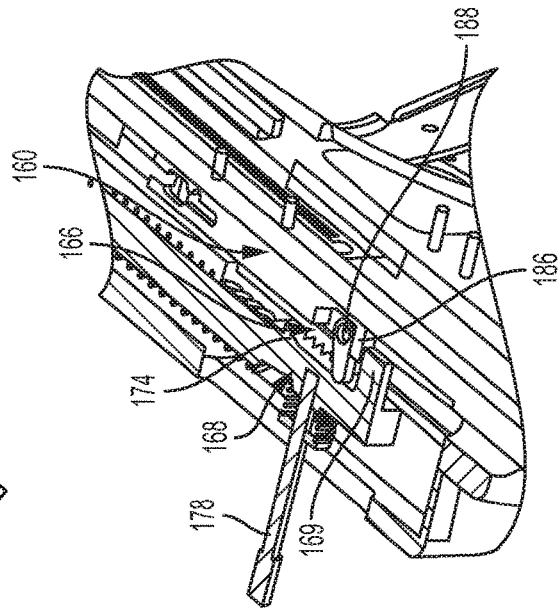
FIG. 15C is another top cross-sectional view of the components of the handle of FIG. 15B, illustrating the method of operating the surgical instrument.
Figure 15B:
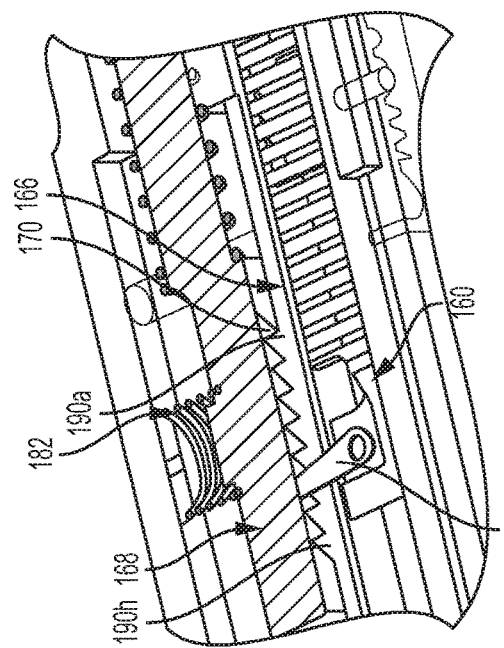
FIG. 15B is another top cross-sectional view of the components of the handle of FIG. 15A, illustrating the method of operating the surgical instrument.

The handle 178 coupled to the sequencer 168 is activated (e.g., retracted and moved distally) to thereby move the sequencer 168 into a pre-activated position. As the sequencer 168 is moved distally, the needle holder 160 is also moved distally as load is applied by the sequencer's stop surface 169 to the proximal end of the needle holder 160 that has the arm 186. As the needle holder 160 moves distally, the needle 107 extends distally into the lower jaw 110 as shown in FIG. 16A. As shown in FIG. 16A, the needle 107 is positioned such that its distal end 107d is proximal to the distal end 110d of the lower jaw 110. As shown by an arrow 191 in FIG. 15A, the sequencer 168 is moved distally such that the tooth 170 of the sequencer 168 is moved distally to a position just distal to a distal-most tooth 190a of the rack 166, as shown in FIG. 15B. The teeth 170 of sequencer 168 thus engage the rack 166 to maintain the position of the stop surface 169 at the proximal end 168p of the sequencer. FIG. 15A illustrates that the rack 166 has eight pairs of teeth 190a, 190b, 190c, 190d, 190e, 190f, 190g, 190h, with each of the pairs including one of the upper teeth 172a and one of the lower teeth 172b of the rack 166. FIG. 15C, showing the surgical instrument 102 at a different cross-section than a cross-section in FIGS. 15A and 15B, additionally illustrates a position of the ramp feature 174 of the sequencer 168 when the sequencer 168 is in the pre-activated position.

FIG. 16A schematically illustrates that, after the needle 107 is advanced distally, the suture magazine 120 attached to the suture magazine carrier 122 is coupled to lower jaw 110 of the surgical instrument 102, as shown by an arrow 189 in FIG. 16B. The suture magazine 120 has the suture 121 releasably coupled thereto, and the suture magazine 120 is coupled to the lower jaw 110 using retaining and positioning features, as discussed above. After the suture magazine 120 is seated in the lower jaw 110, the suture magazine carrier 122 is separated from the suture magazine 120, as shown by an arrow 193 in FIG. 16C.

After the suture magazine 120 is loaded onto the lower jaw, the suture passing needle 107 extends through the longitudinal channel 114 of the lower jaw 110 such that its suture retaining feature 109 is facing the suture magazine 120 and the surgical instrument 102 is activated to load the suture 121 coupled to the suture magazine 120 to the suture passing needle 107. Thus, the trigger 152 can be activated to advance the suture passing needle 107 further distally such that it extends through the keying feature 115 (FIG. 4A) and beyond the distal end of the distal tip 103 of lower jaw 110. This activation of the surgical instrument 102 can be referred to as a "dry fire" since it is performed to load a first portion (e.g., a loop) of the suture 121 onto the needle 107. The dry fire operation can be performed when the surgical instrument 102 is outside of a patient's body. Alternatively, the surgical instrument 102 can be activated to load a suture to the needle when the surgical instrument 102 is inside the patient's body, for example, when the distal end of the surgical instrument 102 is disposed in a joint space or other body cavity, such that the needle advanced beyond the distal end does not traumatize any tissues.

FIGS. 17A-17F illustrate interaction between the sequencer 168, rack 166, and the needle holder 160 during activation of the surgical instrument 102 for the dry firing. As shown in FIG. 17A, activation of the trigger 152 (e.g., as it is squeezed toward the stationary handle 153) causes the needle holder 160 to advance distally, in a direction shown by an arrow 195 in FIG. 17A. As a result, the toggle 188 of the needle holder 160 engages with the trip ramp 175 of the ramp feature 174 of the sequencer 168 and applies a biasing force thereto in a direction shown by an arrow 197 in FIG. 17A. As a result of the toggle 188 pushing the trip ramp 175, the teeth 170 of the sequencer 168 disengage from the rack 166 as the needle holder 160 moves distally, as shown in FIG. 17B. As the toggle 188 clears the ramp feature 174 and is positioned distally thereof, as shown in FIG. 17C, the second spring 182 biases the sequencer 168 proximally, as shown by an arrow 199, and the first spring 180 biases the teeth 170 of the sequencer 168 back towards the rack 166, as shown by an arrow 201, to engage the rack 166 at a next position.

FIG. 17D illustrates the teeth 170 of the sequencer 168 engaged in a different position with the rack 166 as a result of the activation of the firing trigger 152. In particular, the teeth 170 of the sequencer 168, previously engaged proximal to the teeth 190a, are now engaged with the first (proximal-most) and second teeth 190a, 190b of the rack 166. Once the sequencer 168 is positioned at the next position with respect to the rack 166 as shown in FIG. 17D, the stop surface 169 of the sequencer 168 is positioned so as to define a position of the needle holder 160 as the needle holder 160 moves proximally after being advanced distally. In particular, as shown in FIG. 17E, as the firing trigger 152 is released after the needle 107 has been advanced distally, the needle holder 160 returns proximally towards the stop surface 169 of the sequencer 168. As the needle holder 160 moves proximally, the toggle 188 is moved into a recess 192 in the needle holder 160 and is thus prevented from affecting the position of the sequencer 168 (i.e., the toggle 188 is prevented from interacting with the ramp feature 174 of the sequencer 168). The third (e.g. a torsional spring) spring 183 biases the toggle 188 proximally out of recess 192 as the needle holder 160 moves proximally to abut the stop surface 169, as shown in FIG. 17F. In this configuration, the surgical instrument 102 can again be activated to advance the needle distally. Because the needle 107 has been loaded with the suture, as discussed in more detail below, the surgical instrument 102 can be used to apply a first portion of the suture loaded onto the needle 107 to tissue.

Figure 18A:
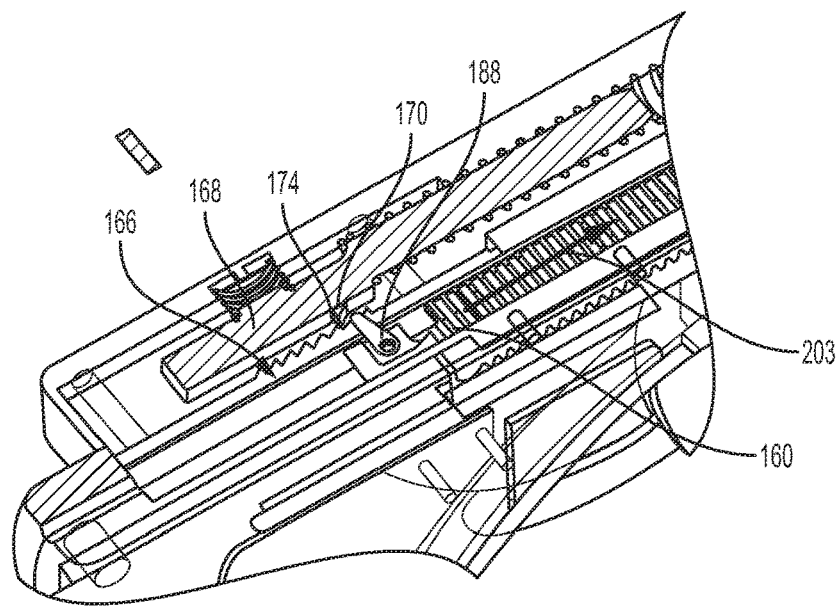
FIG. 18A is a top, partially cross-sectional view of components of the handle of the surgical instrument of FIG. 1, illustrating a method of operating the surgical instrument.
Figure 18B:
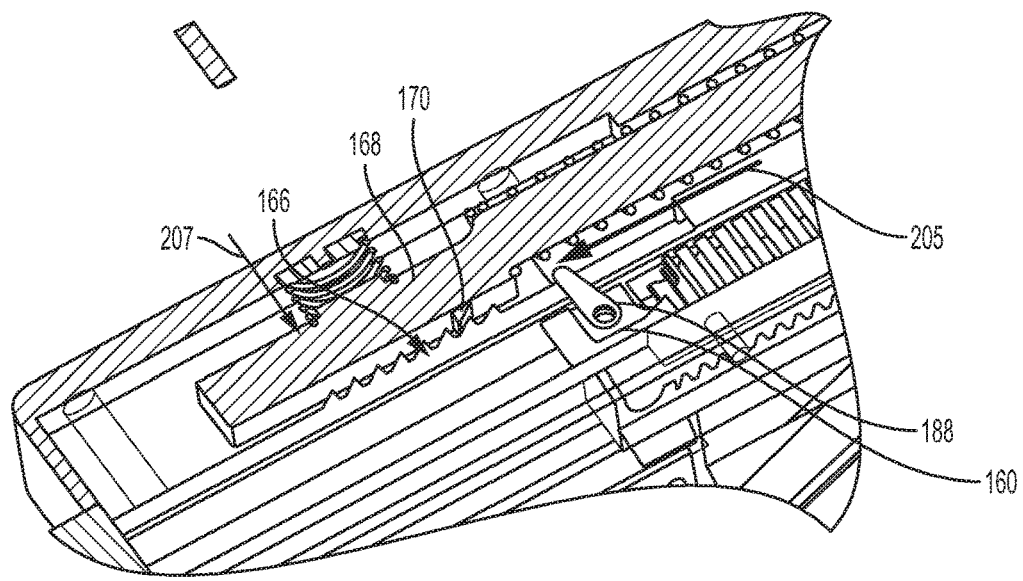
FIG. 18B is another top, partially cross-sectional view of the components of the handle of FIG. 18A, illustrating the method of operating the surgical instrument.
Figure 18C:
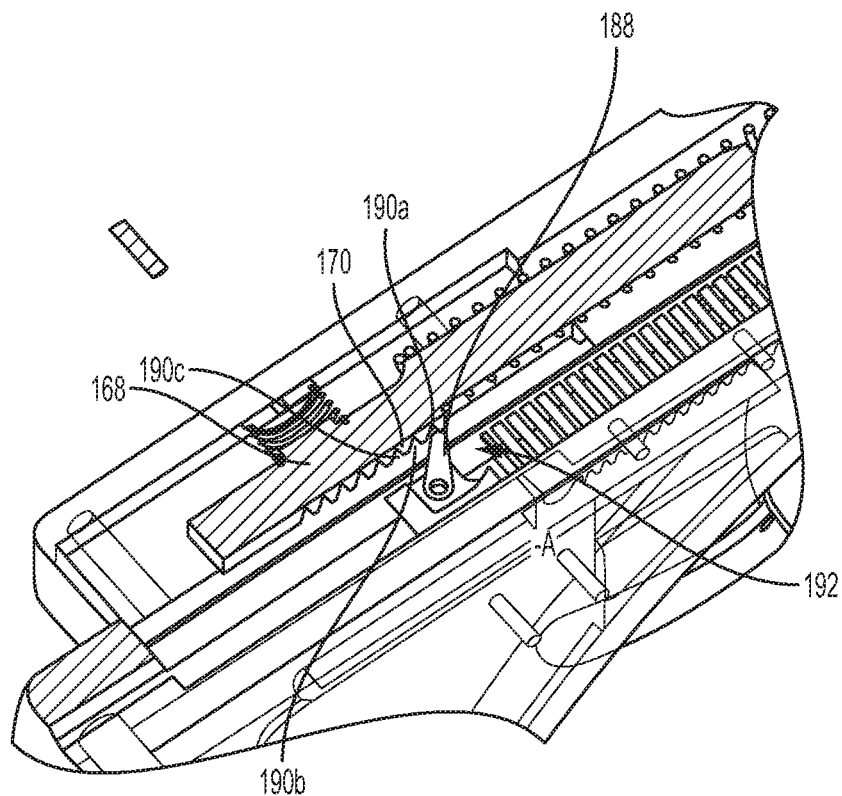
FIG. 18C is a top, partially cross-sectional view of the components of the handle of FIG. 18B, illustrating the method of operating the surgical instrument.
Figure 18D:
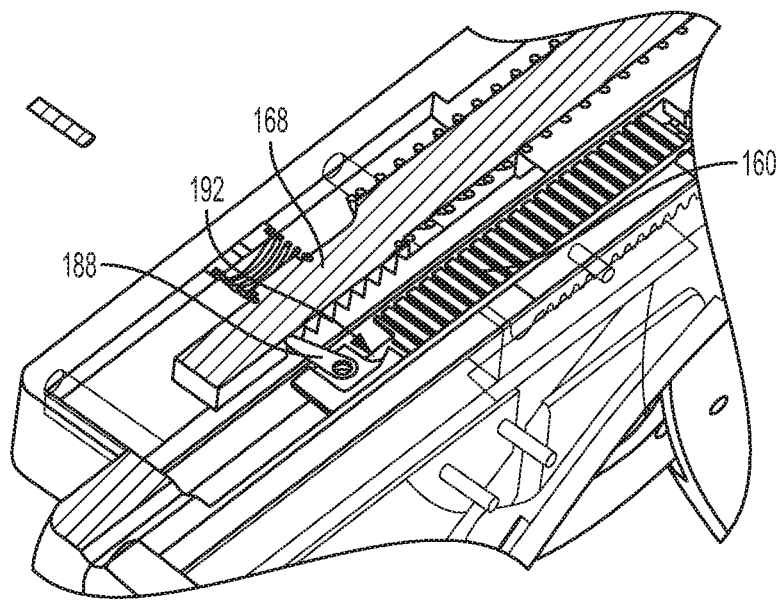
FIG. 18D is a top, partially cross-sectional view of the components of the handle of FIG. 18C, illustrating the method of operating the surgical instrument.

FIGS. 18A-18D illustrate operation of the surgical instrument 102 once it is activated to advance the suture passing needle 107 distally to pass the needle 107 and the suture couple thereto (e.g., the first portion of the suture) through tissue. Thus, as shown in FIG. 18A, activation of the trigger 152 causes the needle holder 160 to advance distally, in a direction shown by an arrow 203. The toggle 188 of the needle holder 160 engages with the trip ramp 175 of the ramp feature 174 of the sequencer 168 and applies a biasing force thereto to thus cause the teeth 170 of the sequencer 168 to disengage from the rack 166, as shown in FIG. 18A. As the toggle 188 clears the ramp feature 174, the second spring 182 biases the sequencer 168 proximally (shown by an arrow 205) and the first spring 180 causes the teeth 170 of the sequencer 168 back towards the rack 166, as shown by an arrow 207, to engage the rack 166 at a next position. FIG. 18C shows the teeth 170 of the sequencer 168 engaged with the second and third teeth 190b, 190c of the rack 166. As the firing trigger 152 is released and the needle holder 160 thereby returns proximally, the third spring 183 biases the toggle 188 proximally. As a result, the toggle 188, which moves into the recess 192 to prevent its engagement with the sequencer 168 (e.g., as shown in FIG. 17E for the previous activation of the instrument 102), is positioned as shown in FIG. 18 D to abut the stop surface 169 (the cross-section of the surgical instrument 102 does not show the stop surface 169). In this configuration, the surgical instrument 102 can be activated to advance the needle distally and apply a second portion of the suture to the tissue.

In the illustrated embodiments, as discussed above, as the needle 107 is retracted proximally following its distal advancement, a portion of a suture, such as suture 121 in FIG. 7, coupled to the suture magazine 120, is loaded onto the needle 107. FIGS. 19A-19D illustrate a process of loading the suture 121 onto the suture passing needle 107 extending through the lower jaw 110. FIG. 19A shows schematically the suture magazine 120 with the plurality of suture loops 150 (also shown in FIG. 7) coupled thereto prior to the needle 107 being loaded with the suture. In particular, in FIG. 19A, the needle 107 is shown as it returns proximally (arrow 209) after the dry firing of the surgical instrument 102 as shown in FIGS. 17A-17F. As also shown in FIG. 19A, in this position, the needle 107 is not yet loaded with the suture.

As shown in FIG. 19B, as the suture passing needle 107 moves further proximally, a protruding edge 194 thereof that is adjacent the suture retaining feature 109 of the needle 107 and faces the suture magazine 120, engages a first portion of the suture 121, such as a first suture loop 150a of the suture loops 150. The compression on the suture 121 between the suture magazine 120 and the side of the needle 107 facing the suture magazine 120 allows the suture 121 to "relax" into the suture retaining feature 109 as the needle 107 moves along a suture-retaining feature 130a of the suture-retaining features 130 (e.g., slots) of the suture magazine 120. In such a relaxed state, the first suture loop 150a is caused to move into the suture retaining feature 109 of the needle 107. As the needle 107 retracts further proximally, a first protrusion 131a of the protrusions 131 between the suture-retaining features 130 of the suture magazine 120 engages the first suture loop 150a and causes it to move deeper into the suture retaining feature 109, as shown in FIG. 19C.

FIG. 19D shows the needle 107 with the first suture loop 150a loaded into the suture retaining feature 109 of the needle 107. The needle 107 is shown in FIG. 19D in the position at which the needle holder 160 seating the needle 107 abuts the stop surface 169 of the sequencer 168 (as shown in FIG. 17F). The needle 107 is thus prevented from moving further proximally. The surgical instrument 102 can be activated to advance the needle 107 distally to pass the first suture loop 150a coupled to the needle 107 through tissue.

After the needle 107 is advanced distally and passed through the tissue after the firing of the surgical instrument 102, the needle 107 is then retracted proximally. As the needle 107 moves proximally, it picks up the subsequent portion of the suture 121, such as a second suture loop 150b of the suture loops 150. FIGS. 20A to 20D illustrate a process of loading the second suture loop 150b to the needle 107 after the dry firing of the surgical instrument 102 to load the suture (e.g., the first suture loop 150a) onto the needle 107. FIG. 20A shows the needle 107 being advanced distally (arrow 211) to pass the first suture loop 150a through tissue. After the first suture loop 150a is applied to the tissue, the needle 107 returns proximally, as shown by arrow 213 in FIG. 20B. The subsequent, second suture loop 150b is loaded onto the needle 107, similar to the way in which the first suture loop 150a was loaded, as shown in FIGS. 20C and 20D. FIG. 20D shows the needle 107 at the position in which it abuts the stop surface 169 of the sequencer 168 and is thus ready to be fired distally to apply the second suture loop 150b coupled thereto to tissue.

The suture passing surgical instrument described herein can be used in a surgical method for passing suture through tissue such that jaws of the surgical instrument remain in the patient's body without the need to be removed after each act of passing a length of suture through tissue. The method involves positioning first and second jaws of the suture passing surgical instrument such that the jaws grasp tissue within a body of a patient, and repeatedly activating the surgical instrument to cause a needle to move along a longitudinal channel extending through one of the jaws such that the needle is advanced distally to pass through the tissue to pass a suture loop coupled to the needle with each activation of the needle. Following each passage through the tissue, the jaws remain in the body, the needle is retracted proximally, and a subsequent suture loop is loaded onto the needle.

Figure 21A:
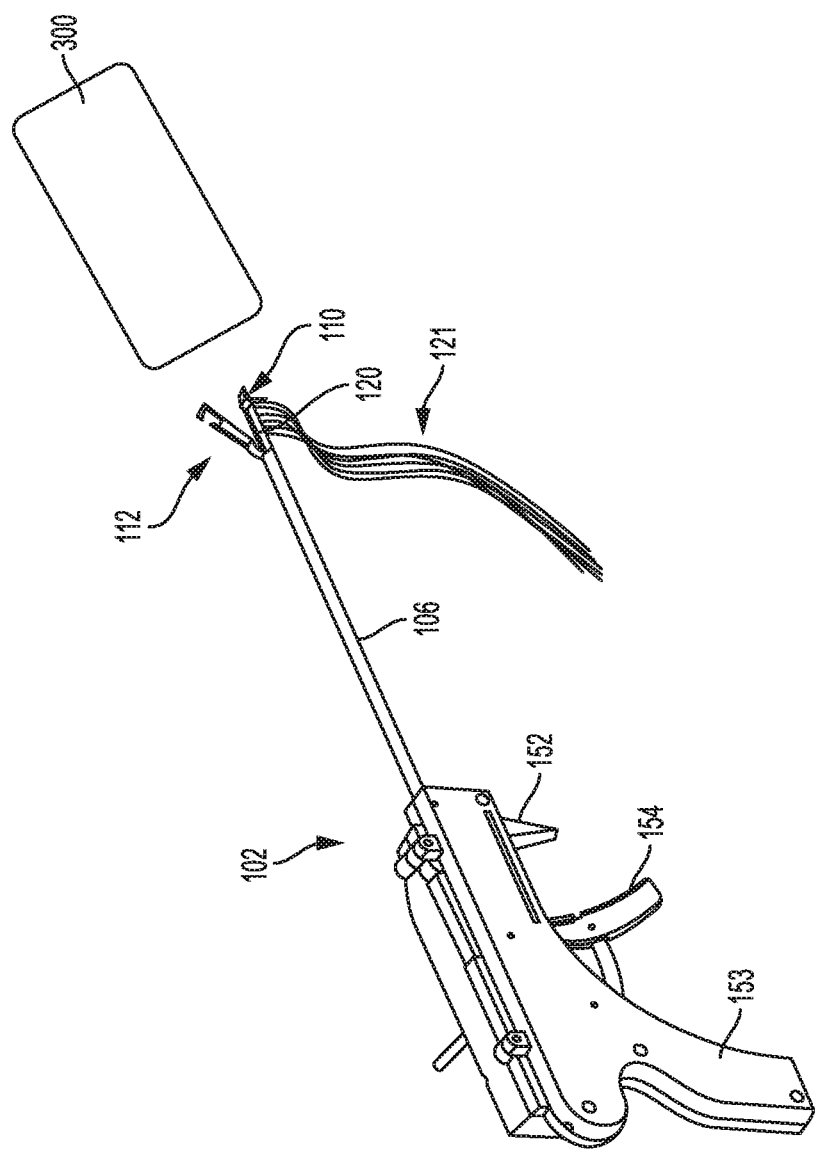
FIG. 21A is a perspective view of one embodiment of a surgical instrument, illustrating jaws of the surgical instrument positioned adjacent to a tissue within a body of a patient during a surgical method.

FIGS. 21A to 21F illustrate one embodiment of a surgical method for passing suture through tissue during a surgical procedure. The method can be performed using the surgical instrument 102 described herein, though it should be appreciated that other suitable suture passing surgical instrument can be used. As shown in FIG. 21A, the surgical instrument 102 can be configured to pass the suture 121 coupled to the suture magazine 120 through tissue 300. The surgical instrument 102 shown in FIG. 21A can be in the configuration ready to apply a first portion of the suture 121 (e.g., the first suture loop 150a) to the tissue 300. The first suture loop 150a is loaded onto the needle 107 prior to positioning the lower and upper jaws 110, 112 of the surgical instrument 102 so as to grasp the tissue 300, as a result of the dry firing of the surgical instrument 102. Although not shown in FIGS.

21A to 21F, the surgical instrument 102 is disposed in the patient's body through a surgical access port such as a cannula or a similar device as is typically used in minimally invasive surgical procedures such as arthroscopic surgery. As explained above, it is understood that the jaws 110, 112 remain in the body as subsequent portions of the suture are loaded onto the needle.

Figure 21B:
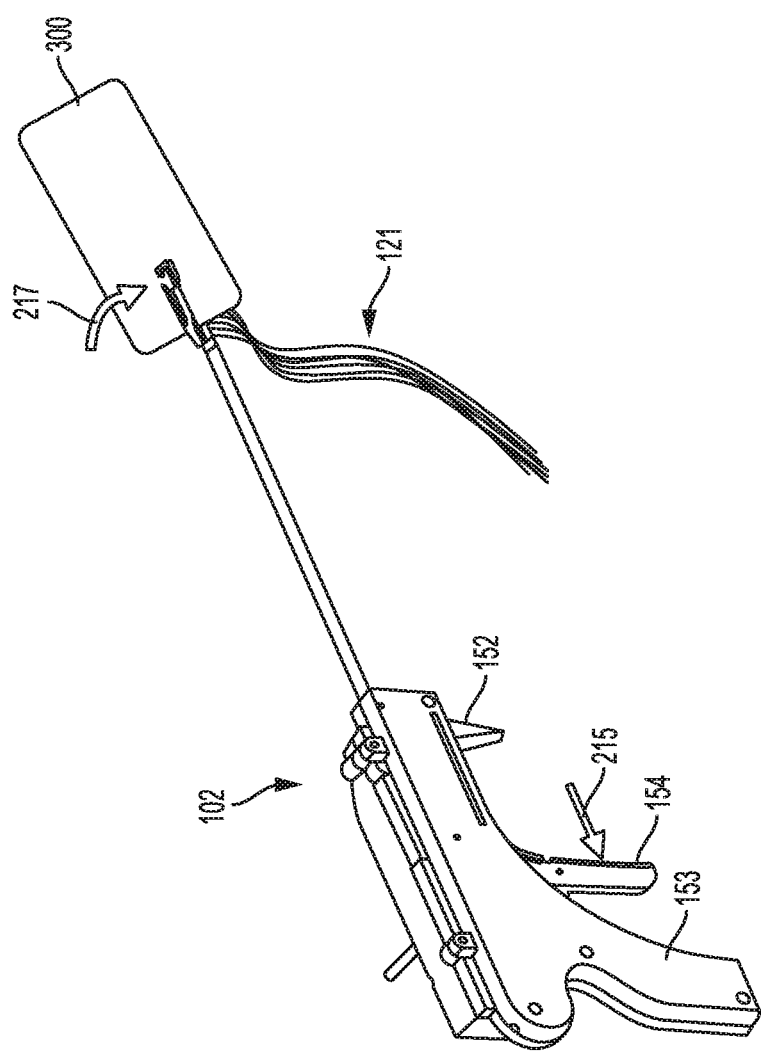
FIG. 21B is another perspective view of the surgical instrument of FIG. 21A, illustrating the jaws of the surgical instrument grasping the tissue at a first location.
Figure 21C:
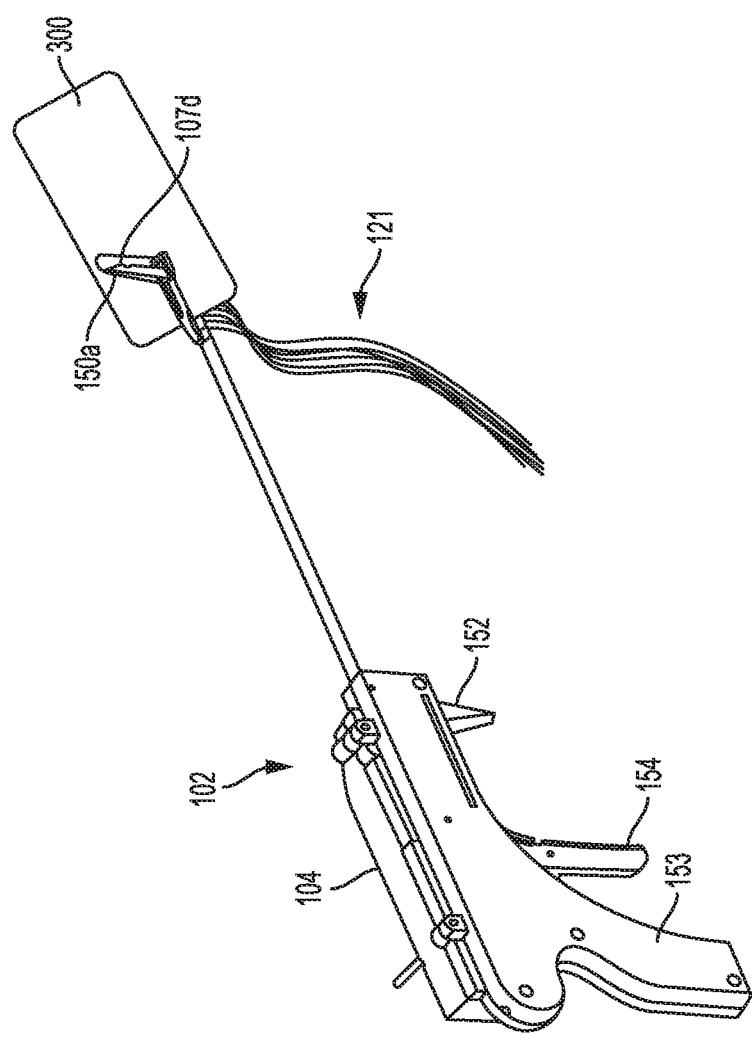
FIG. 21C is another perspective view of the surgical instrument of FIG. 21B, illustrating a needle of the surgical instrument passing a first suture loop through the tissue at the first location.

FIG. 21B illustrates the tissue 300 positioned between the lower and upper jaws 110, 112 of the surgical instrument 102. Once the jaw approximation trigger 154 is activated, such as being moved (arrow 215) towards the stationary handle 153, the lower and upper jaws 110, 112 approximate to thereby clamp the tissue 300 therebetween. In FIG. 21B, the lower and upper jaws 110, 112 grasp the tissue 300 at a first location of the tissue 300. FIG. 21C illustrates the needle 107 advanced distally as the firing trigger 152 is activated, such that the distal end 107d of the needle 107 is passed through the tissue 300 at the first location and the first suture loop 150a is thereby passed through the tissue. As discussed above, as the needle 107 moves proximally, the next portion of the suture, such as the second suture loop 150b, becomes loaded onto the needle 107.

Figure 21D:
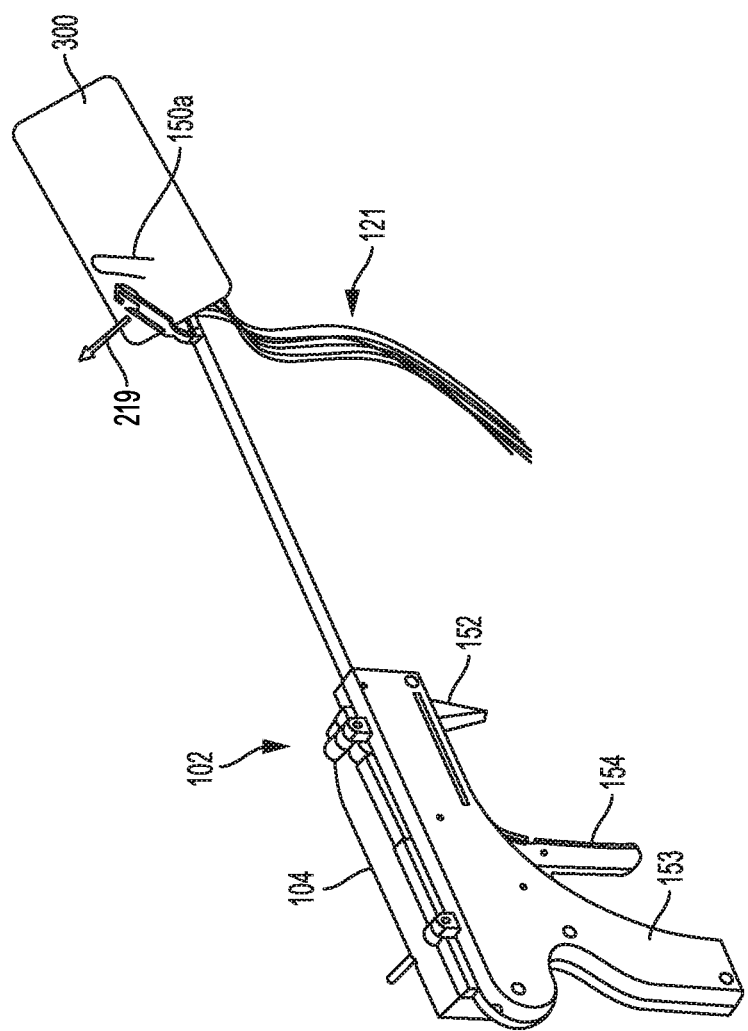
FIG. 21D is another perspective view of the surgical instrument of FIG. 21C, illustrating the jaws in the open position after the first suture loop has been passed through the tissue.
Figure 21E:
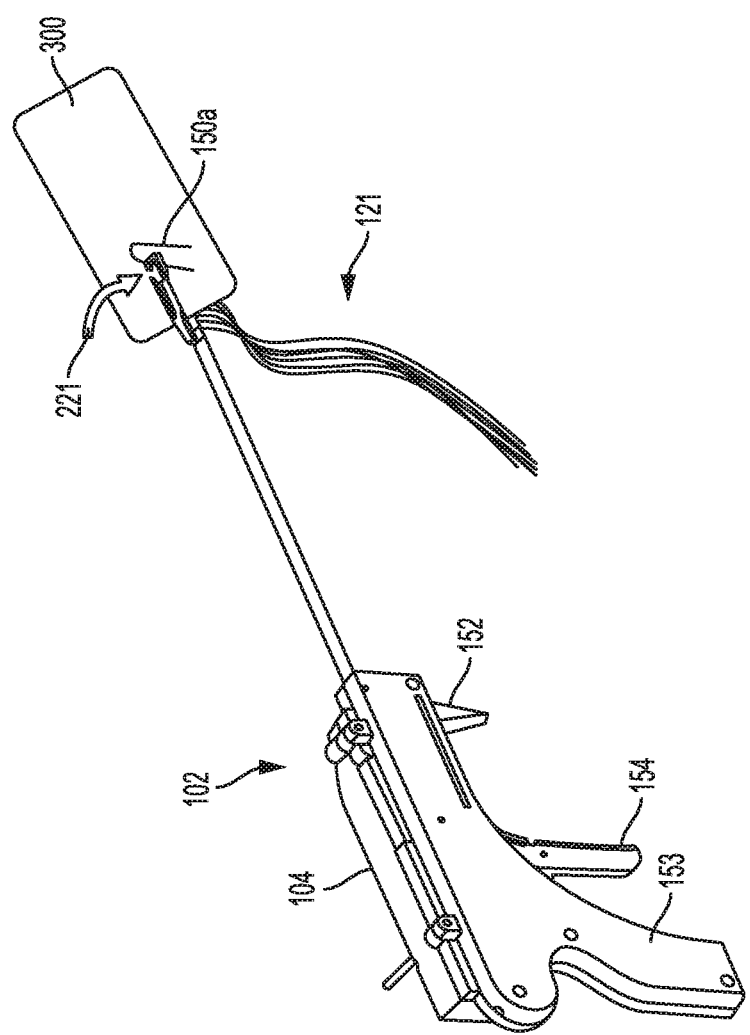
FIG. 21E is another perspective view of the surgical instrument of FIG. 21D, illustrating the jaws grasping the tissue at a second location.

FIG. 21D shows the first suture loop 150a having been applied to the tissue and the lower and upper jaws 110, 112 moved to an open position (arrow 219) as the tissue release trigger 156 of the surgical instrument 102 (shown in FIG. 2) is activated. The surgical instrument 102 is then repositioned, while being maintained in the patient's body, such that the lower and upper jaws 110, 112 are disposed around the next location in the tissue 300. FIG. 21E illustrates the lower and upper jaws 110, 112 clamped (arrow 221) over the tissue 300 at the next (second) location at which the suture is to be applied to the tissue 300.

Figure 21F:
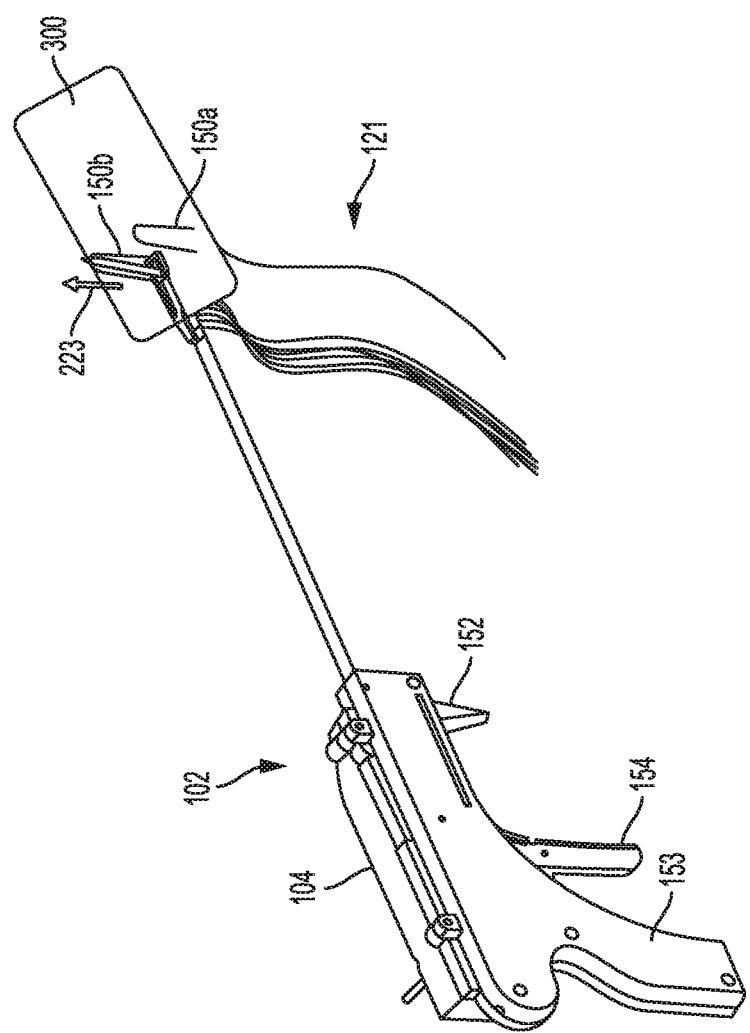
FIG. 21F is another perspective view of the surgical instrument of FIG. 21E, illustrating the needle passing a second suture loop through the tissue at the second location.
Figure 21G:
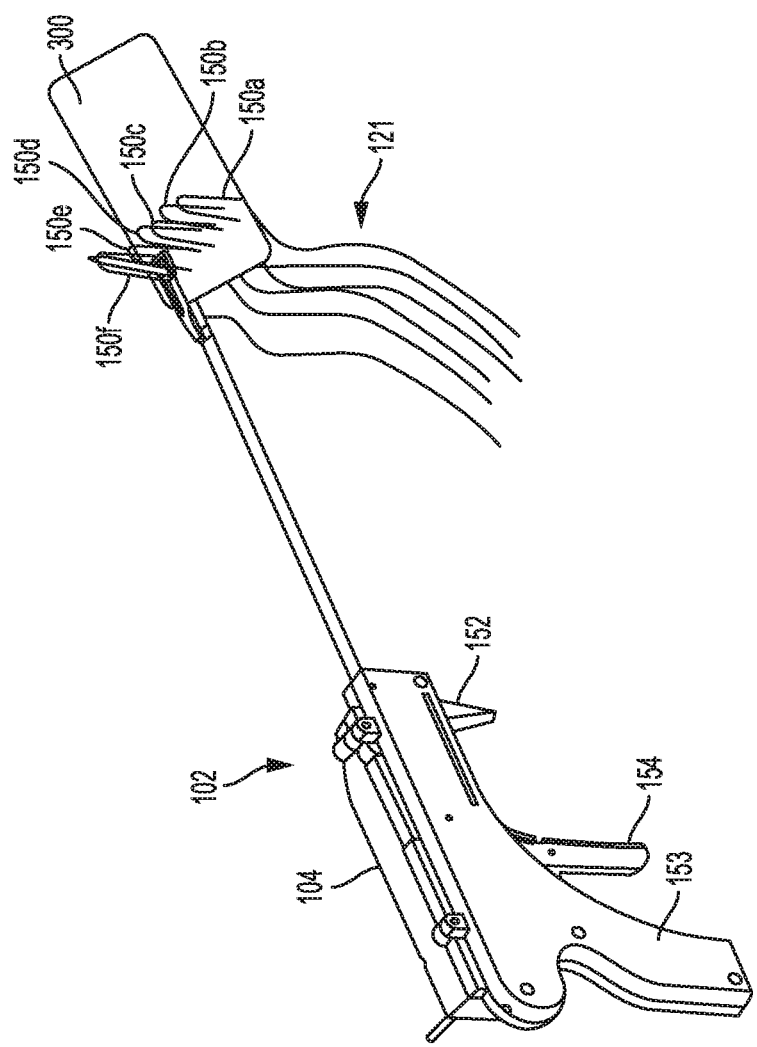
FIG. 21G is another perspective view of the surgical instrument of FIG. 21F, illustrating suture loops passed through the tissue at multiple locations and the needle passing a suture loop through the tissue.

FIG. 21F illustrates the needle 107 again advanced distally (arrow 223) as the firing trigger 152 is activated, such that the distal end 107d of the needle 107 is passed through the tissue 300 at the next location, and the second suture loop 150b is thereby passed through the tissue 300. As discussed above, as the needle 107 returns proximally, the next portion of the suture, such as the third suture loop 150c, is loaded onto the needle 107. The process of applying the suture 121 to the tissue 300 can be continued in a similar manner, and FIG. 21G illustrates five suture loops 150a to 150e applied to the tissue 300, with the surgical instrument 102 in the process of applying the sixth suture loop 150f to the tissue 300. The suture magazine 120 can be separated from the jaw after the last portion of the suture, such as the suture loop, has been applied to the tissue. It should be appreciated that, as noted above, the suture magazine 120 is shown to have six suture loops 150a to 150f removably coupled thereto by way of example only, as the suture magazine can have releasably coupled thereto any suitable number of suture loops that can be formed by any number of suture strands. It should also be appreciated that portions of the suture do not have to form loops, and the suture can be otherwise coupled to the suture magazine 120. Regardless of the type of the suture and the way in which it is coupled to the suture magazine, portions of the suture become loaded onto the needle with each activation of the needle without taking the jaws out of the patient's body.

In some embodiments, one or more portions of a suture, coupled to a suture holding construct including a suture magazine and a suture magazine carrier, can be coupled to a suture anchor. The suture can be coupled to the suture anchor prior to or after the suture is coupled to the suture magazine. Furthermore, the suture holding construct can be coupled to a suture anchor delivery device such that the suture, which is coupled to the suture holding construct, is also coupled to the suture anchor delivery device. For example, the suture holding construct can be coupled to a handle of the suture anchor delivery device and the suture can extend along a length of a shaft of the suture anchor delivery device. In this way, the suture anchor having the suture coupled thereto can be inserted into a bone. The suture holding construct, also coupled to the suture, can then be transferred from the suture anchor delivery device to a jaw of a surgical instrument for use in passing suture through tissue. The suture magazine carrier can then be separated from the suture magazine coupled to the jaw, as discussed above, and the surgical instrument can be used to pass the suture through tissue to thereby repair a defect. This allows improved suture management and a simplified, less error-prone transfer of the suture to tissue.

Figure 22:
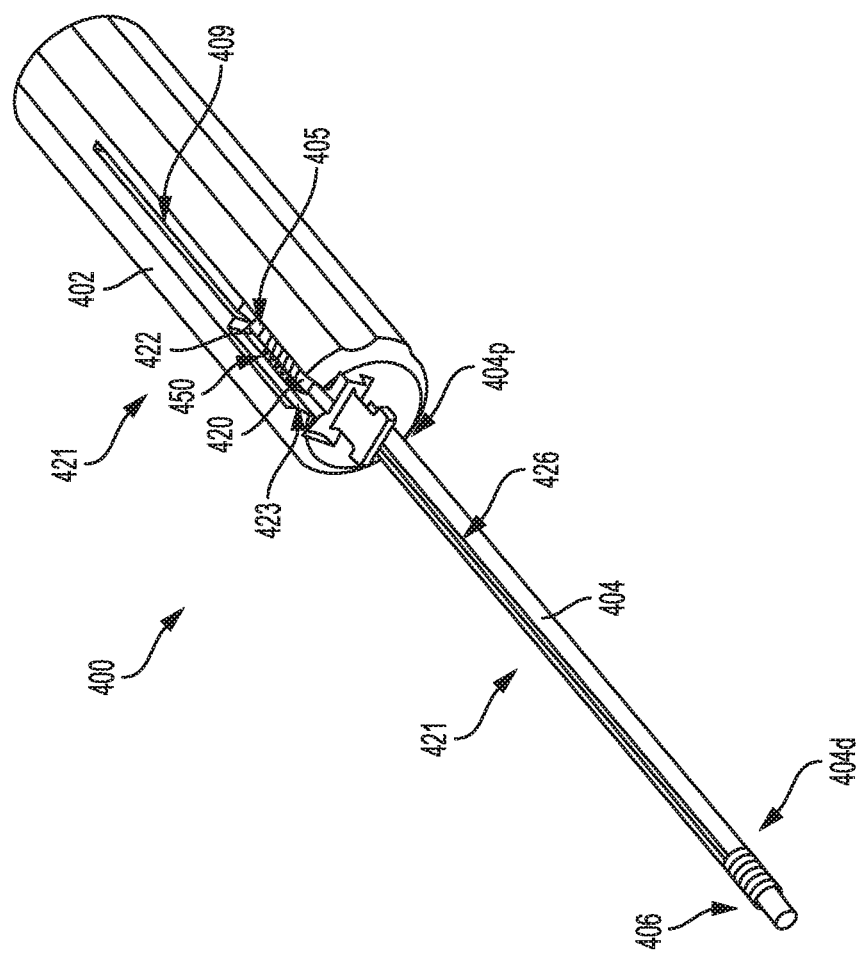
FIG. 22 is a perspective view of one embodiment of a suture anchor delivery device having a suture holding construct removably coupled thereto.
Figure 23:
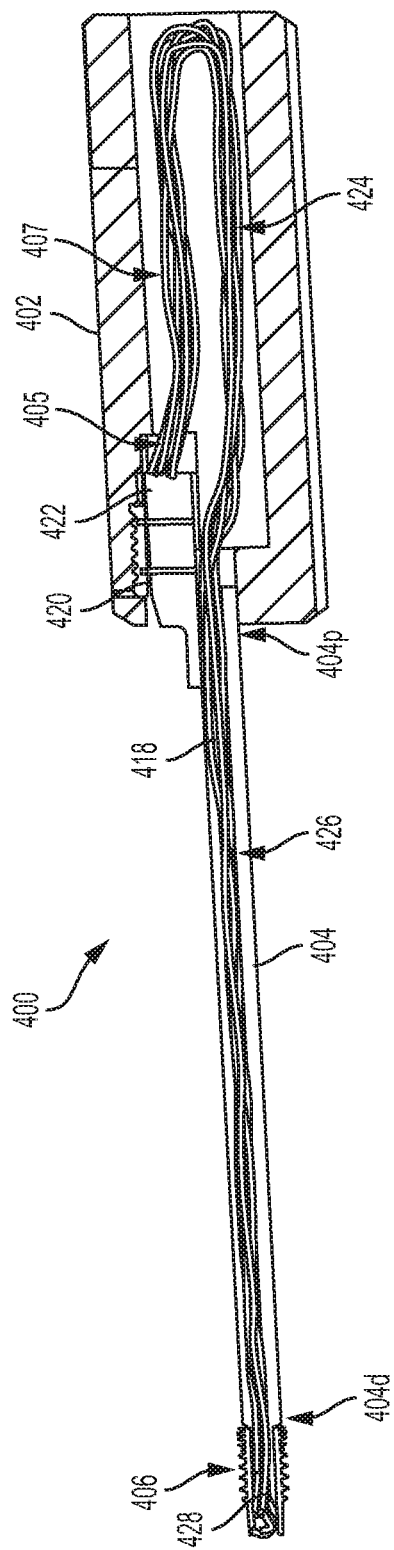
FIG. 23 is a side cross-sectional view of the suture anchor delivery device of FIG. 22.

FIGS. 22 and 23 show an anchor driver or suture anchor delivery device 400 including a proximal handle 402 and an elongate shaft 404 extending distally therefrom and having a suture anchor 406 coupled to a distal end 404d thereof. As shown by way of example, the proximal handle 402 can have a cavity 405 in an outer wall thereof, the cavity 405 configured to seat a suture holding construct 423 including a suture magazine carrier 422 and a suture magazine 420 coupled thereto. It should be appreciated that the cavity 405, or any other suitable feature, can have any suitable configuration.

The suture 421 can encompass one or more suture strands. As shown in FIGS. 22 and 23, the suture 421 can includes a plurality of suture loops 450 (or portions of the suture having another form) disposed around the suture magazine carrier 422 and the suture magazine 420, a proximal portion 424 disposed in a cavity 407 in the handle 402, and a distal portion 426 disposed in a longitudinal cavity 418 extending between distal and proximal ends 404d, 404p of the shaft 404. As shown in FIG. 23, the cavity 407 in the handle 402 can communicate with a longitudinal slot 409 in the handle 402 through which the distal portion 426 of the suture 421 can be removed from the handle 402. The cavities 405 and 407 of the handle 402, which can have any suitable configuration, communicate with one another and at least the cavity communicates with the longitudinal cavity 418 of the shaft 404.

It should be appreciated that the suture anchor delivery device 400 can be any suitable suture anchor delivery device, as the described techniques are not limited to any particular device or its method of operation. In some embodiments, the proximal portion 424 of the suture 421, which is shown in this example disposed in the handle cavity 407, can be disposed in a packaging card or other enclosure, to facilitate its management, particularly when the suture 421 is separated from the delivery device 400.

The distal portion 426 of the suture 421 can extend through at least a portion of a channel 428 extending through the suture anchor 406, and the distal portion 426 can be coupled to the suture anchor 406 in any suitable manner. In one embodiment, distal ends of the distal portion 426 of the suture 421 can extend distally beyond the suture anchor 406. The suture anchor 406 can have any suitable configuration.

Figure 24A:
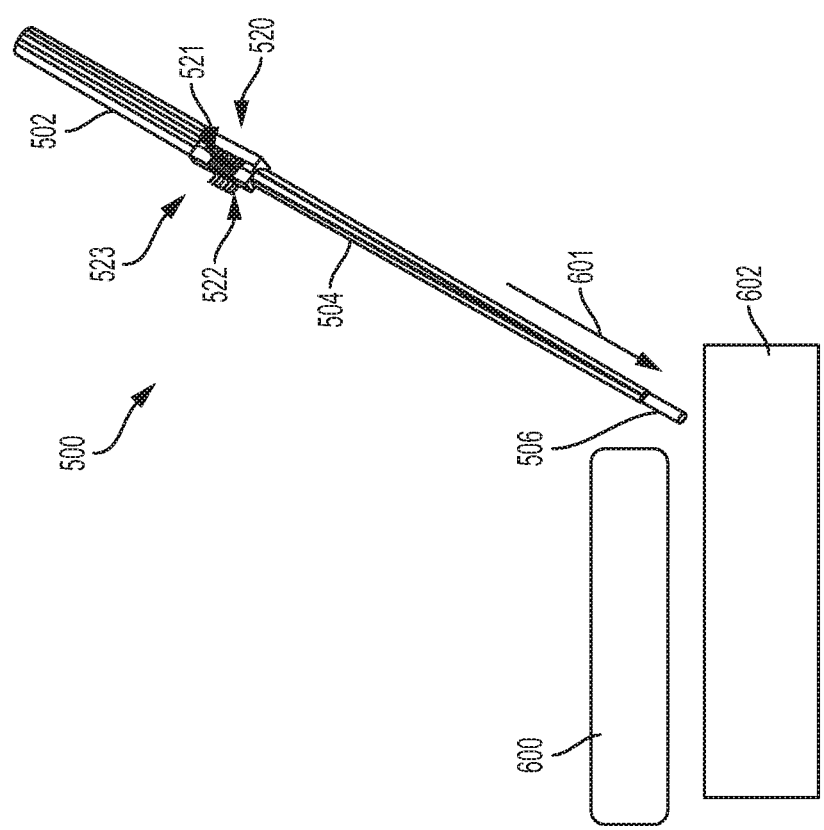
FIG. 24A is a perspective view of one embodiment of a suture anchor delivery device having a suture holding construct removably coupled thereto; illustrating the suture anchor delivery device in proximity to a bone and a tissue to be attached to the bone.
Figure 24B:
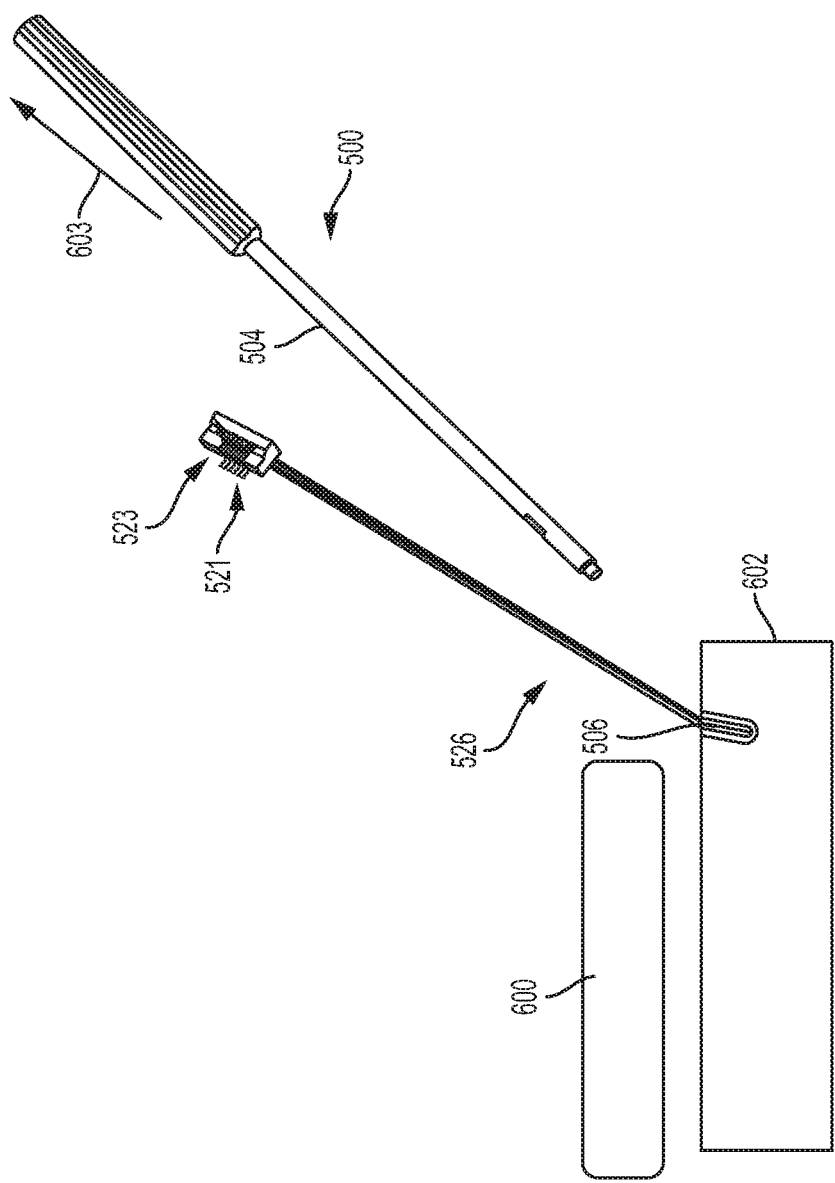
FIG. 24B is another perspective view of the suture anchor delivery device of FIG. 24A, illustrating the suture holding construct being separated from the suture anchor delivery device after a suture anchor has been inserted into the bone using the suture anchor delivery device.
Figure 24C:
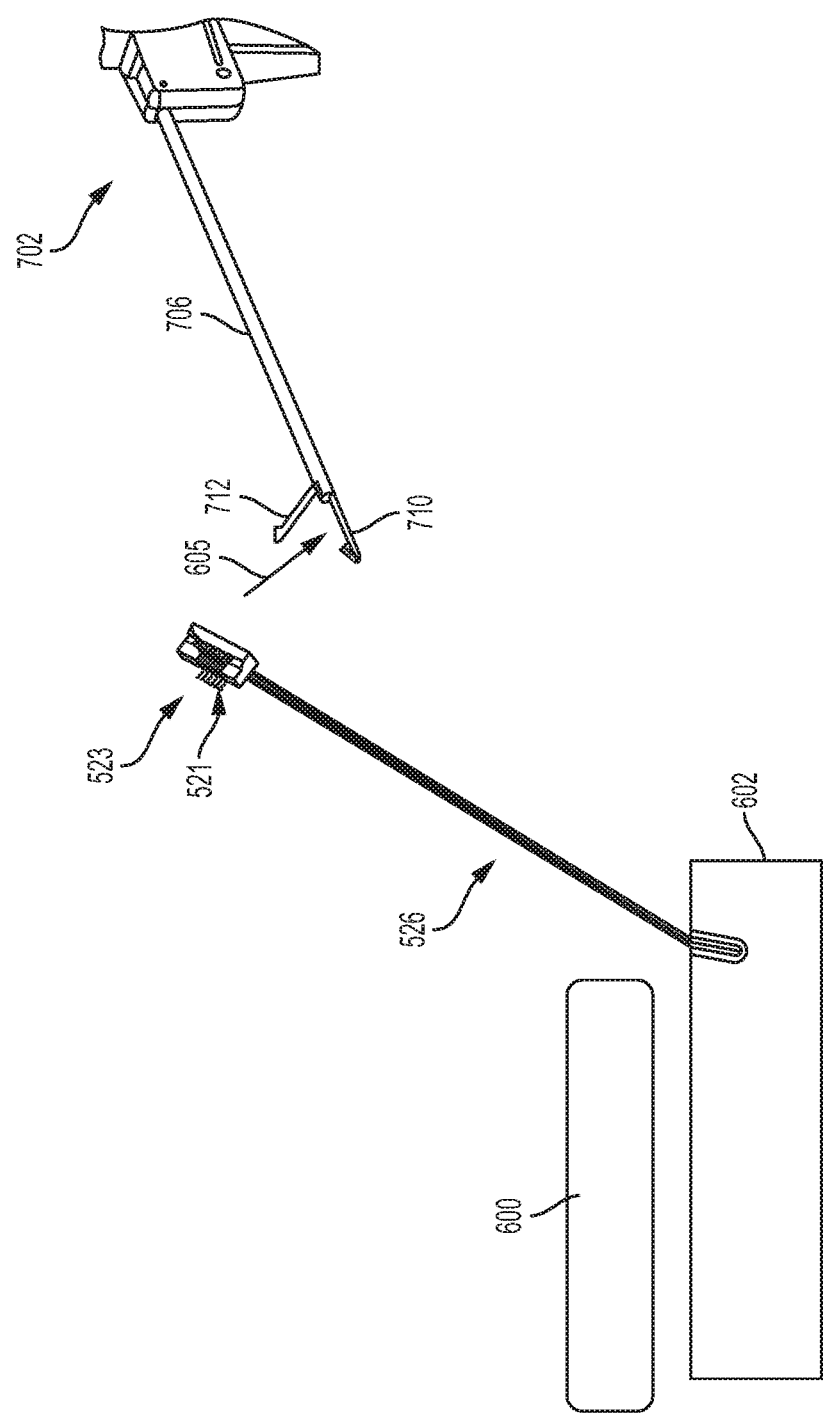
FIG. 24C is another perspective view of the suture anchor delivery device of FIG. 24B, illustrating the suture holding construct being moved to a jaw of a surgical instrument for use in passing suture through tissue.

FIG. 24A to 24C illustrate one embodiment of using a suture anchor delivery device 500 having a suture holding construct 523 coupled thereto, the suture holding construct 523 including a suture magazine carrier 522 and a suture magazine 520. The suture anchor delivery device 500 having a proximal handle 502 and a shaft 504 with a suture anchor 506 at its distal end can be similar to the suture anchor delivery device 400 in FIGS. 22 and 23, though the device 500 can have any other configuration. For example, in the example illustrated in FIGS. 24A to 24C, the suture holding construct 523 is shown to be disposed at least partially beyond an outer surface of the handle 502. A suture 521 can be coupled to the suture holding construct 523 and it can extend through the handle 502 and the shaft 504 similar to the way shown in FIGS. 22 and 23 for the suture holding construct 423 and the suture anchor delivery device 400.

FIG. 24A illustrates the suture anchor delivery device 500 delivered (arrow 601) to a bone 602. A tissue 600 to be coupled to the bone 602 using the suture 521 is also shown. FIG. 24B shows that the suture anchor 506 delivered to the bone 602, which can be done using any suitable technique. As shown, the anchor 506 is coupled to the suture 521 that is coupled to the suture holding construct 523. In this example, the suture 521 is coupled to the anchor 506 such via a distal portion 526 of the suture 521, previously associated with the shaft 504. FIG. 24B illustrates the suture anchor delivery device 500 being removed (arrow 603) from the surgical site after the anchor 506 has been inserted into the bone 602.

FIG. 24C further shows the suture holding construct 523 to be transferred (arrow 605) to a lower jaw 710 of the lower and upper jaws 710, 712 coupled to a shaft 706 of a surgical instrument 702 (only a distal portion is shown). The surgical instrument 702 can be similar to surgical instrument 102 (FIGS. 1 and 2), and the lower jaw 710 can have a configuration similar to that of lower jaw 110 of the surgical instrument 102 discussed above. However, the surgical instrument 702 can have any other suitable configuration. Once the suture holding construct 523 is coupled to the lower jaw 710 of the surgical instrument 702, the suture magazine carrier 522 can be separated from the suture magazine 520 such that the suture 521 remains coupled to the suture magazine 520. The surgical instrument 702 can then be activated to load the suture 521 removably coupled to the suture magazine 520 to a needle of the surgical instrument 702 (not shown) and to pass the suture 521 through the tissue 600 using, for example, the technique as discussed above.

A person skilled in the art will appreciate that the devices, systems, and methods disclosed herein have application in conventional minimally-invasive and open surgical instrumentation as well application in robotic-assisted surgery. In some embodiments, the devices, systems, and methods described herein are provided for open surgical procedures, and in other embodiments, the devices, systems, and methods are provided for arthroscopic, laparoscopic, endoscopic, and other minimally invasive surgical procedures. The devices may be fired directly by a human user or remotely under the direct control of a robot or similar manipulation tool. However, a person skilled in the art will appreciate that the various methods, systems, and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical instrument for use in passing suture through tissue, comprising:
   a suture magazine having a longitudinal slot;
   first and second jaws disposed on a distal end of an elongate shaft and configured to grasp tissue therebetween, the first jaw having a cavity configured to removably and replaceably seat the suture magazine, and the first jaw having a retaining feature configured to mate with a corresponding retaining feature of the suture magazine; and
   a needle selectively movable along a longitudinal channel extending through an outer side wall of the first jaw and having a suture retaining feature that is formed at a distal end thereof and configured to grasp a suture releasably coupled to the suture magazine, wherein the longitudinal slot of the suture magazine is configured to facilitate passage of the needle therethrough.

2. The surgical instrument of claim 1, wherein the retaining feature of the first jaw is configured to mate with a snap feature.

3. The surgical instrument of claim 1, wherein the first jaw has distal and proximal positioning features disposed at distal and proximal ends thereof and configured to mate with corresponding distal and proximal positioning features of the suture magazine to maintain a position of the suture magazine relative to the first jaw.

4. The surgical instrument of claim 1, further comprising a handle disposed at a proximal end of the elongate shaft, the handle having an actuator configured to selectively activate the needle.

5. The surgical instrument of claim 1, wherein the suture retaining feature of the needle comprises a notch.

6. The surgical instrument of claim 1, wherein the suture magazine has at least one suture releasably coupled thereto by forming a plurality of suture loops disposed around a side wall of the suture magazine and along a plurality of suture-retaining features spaced apart along a longitudinal axis of the suture magazine.

7. The surgical instrument of claim 6, wherein the suture-retaining features comprise slots formed in the side wall of the suture magazine.

8. The surgical instrument of claim 6, further comprising a suture magazine carrier removably coupled to the suture magazine.

9. The surgical instrument of claim 8, wherein the suture magazine carrier is configured to seat the suture magazine such that the suture loops are formed around the suture magazine.

10. A surgical system comprising the surgical instrument of claim 8, wherein the suture magazine carrier with the suture magazine removably coupled thereto is coupled to an anchor inserter instrument.

11. A surgical instrument for use in passing suture through tissue, comprising:
   first and second jaws disposed on a distal end of an elongate shaft and configured to grasp tissue therebetween;
   a needle selectively movable along a longitudinal channel extending through an outer side wall of the first jaw and having a notch that is formed therein and is configured to grasp a suture releasably coupled to a suture magazine; and
   a suture magazine configured to releasably mate to the first jaw, the first jaw having a cavity configured to removably and replaceably seat the suture magazine, and the suture magazine including a longitudinal slot configured to facilitate passage of the needle therethrough.

12. The surgical instrument of claim 11, wherein the suture magazine includes a protrusion configured to mate with a protrusion of the first jaw to releasably mate the suture magazine to the first jaw.

13. The surgical instrument of claim 11, wherein the suture magazine has at least one suture releasably coupled thereto by forming a plurality of suture loops disposed around a side wall of the suture magazine, and the suture magazine has a plurality of slots formed in the side wall of the suture magazine and having the at least one suture retained therein.

14. The surgical instrument of claim 11, further comprising a suture magazine carrier removably coupled to the suture magazine.

15. The surgical instrument of claim 14, wherein the suture magazine carrier is configured to seat the suture magazine such that the suture loops are formed around the suture magazine.

16. The surgical instrument of claim 11, wherein the first jaw has distal and proximal positioning features disposed at distal and proximal ends thereof and configured to mate with corresponding distal and proximal positioning features of the suture magazine to maintain a position of the suture magazine relative to the first jaw.

17. The surgical instrument of claim 11, further comprising a handle disposed at a proximal end of the elongate shaft, the handle having an actuator configured to selectively activate the needle.

18. A surgical instrument for use in passing suture through tissue, comprising:
   a suture magazine;
   first and second jaws disposed on a distal end of an elongate shaft and configured to grasp tissue therebetween, the first jaw having a cavity configured to removably and replaceably seat the suture magazine; and
   a needle selectively movable along a longitudinal channel extending through an outer side wall of the first jaw and having a suture retaining feature that is formed at a distal end thereof and configured to grasp a suture releasably coupled to the suture magazine.

19. The surgical instrument of claim 18, wherein the suture magazine has a longitudinal slot that is configured to facilitate passage of the needle therethrough.

20. The surgical instrument of claim 18, wherein the suture magazine includes a protrusion configured to mate with a protrusion of the first jaw when the suture magazine is seated in the cavity.

* * * * *